United States Patent
Matsuura et al.

(10) Patent No.: US 10,711,247 B2
(45) Date of Patent: Jul. 14, 2020

(54) METHOD FOR REDUCING PLURIPOTENT STEM CELLS, METHOD FOR PRODUCING CELL POPULATION HAVING REDUCED PLURIPOTENT STEM CELLS

(71) Applicant: TOKYO WOMEN'S MEDICAL UNIVERSITY, Tokyo (JP)

(72) Inventors: Katsuhisa Matsuura, Tokyo (JP); Tatsuya Shimizu, Tokyo (JP); Hiroyoshi Seta, Tokyo (JP)

(73) Assignee: TOKYO WOMEN'S MEDICAL UNIVERSITY, Tokyo (JP)

( * ) Notice: Subject to any disclaimer, the term of this patent is extended or adjusted under 35 U.S.C. 154(b) by 48 days.

(21) Appl. No.: 15/755,293

(22) PCT Filed: Aug. 23, 2016

(86) PCT No.: PCT/JP2016/074545
§ 371 (c)(1),
(2) Date: Feb. 26, 2018

(87) PCT Pub. No.: WO2017/038562
PCT Pub. Date: Mar. 9, 2017

(65) Prior Publication Data
US 2018/0245047 A1    Aug. 30, 2018

(30) Foreign Application Priority Data

Aug. 31, 2015 (JP) .................. 2015-171230

(51) Int. Cl.
*C12N 5/077* (2010.01)
*C12N 5/074* (2010.01)
*C12N 15/09* (2006.01)
*C12N 5/10* (2006.01)

(52) U.S. Cl.
CPC ......... *C12N 5/0657* (2013.01); *C12N 5/0696* (2013.01); *C12N 5/10* (2013.01); *C12N 15/09* (2013.01); *C12N 2501/998* (2013.01); *C12N 2502/1329* (2013.01); *C12N 2502/45* (2013.01); *C12N 2506/45* (2013.01); *C12N 2523/00* (2013.01)

(58) Field of Classification Search
CPC .. C12N 2501/998; C12N 5/00; C12N 5/0657; C12N 5/0696; C12N 2502/1329
See application file for complete search history.

(56) References Cited

U.S. PATENT DOCUMENTS

2014/0056859 A1  2/2014  Okano et al.
2015/0297794 A1  10/2015  Yamashita et al.

FOREIGN PATENT DOCUMENTS

| WO | 2012/133945 A1 | 10/2012 |
| WO | 2013/137491 A1 | 9/2013 |
| WO | 2015/112581 A1 | 7/2015 |

OTHER PUBLICATIONS

Matsuura et al., "TRPV-1-mediated elimination of residual iPS cells in bioengineered cardiac cell sheet tissues," Scientific Reports, Feb. 18, 2016, 6:21747, DOI:10.1038/srep21747, 13 pages.
Qi et al., "Role of TRPV1 in the Differentiation of Mouse Embryonic Stem Cells into Cardiomyocytes," PLoS One, Jul. 24, 2015, 10(7): e0133211. doi:10.1371/journal.pone.0133211, 12 pages.
International Application No. PCT/JP2016/074545, International Search Report dated Nov. 22, 2016, 1 page.
Matsuura et al., "Elimination of Remaining Undifferentiated Induced Pluripotent Stem Cells in the Process of Human Cardiac Cell Sheet Fabrication Using a Methionine-Free Culture Condition," Tissue Engineering: Part C, Mar. 2015, vol. 21, No. 3, pp. 330-338, DOI: 10.1089/ten.tec.2014.0198.

*Primary Examiner* — Ruth A Davis
(74) *Attorney, Agent, or Firm* — Kilpatrick Townsend & Stockton LLP

(57) ABSTRACT

The present invention pertains to a method for culturing a cell population including pluripotent stem cells and differentiated cells derived from pluripotent stem cells at a temperature of 40.5° C. or higher and reducing the pluripotent stem cells included in the cell population. The present invention also pertains to a method for reducing pluripotent stem cells from a cell population including pluripotent stem cells and differentiated cells derived from pluripotent stem cells, wherein the method includes a step for activating the TRPV-1 expressed in the pluripotent stem cells included in the cell population. The present invention makes it possible to reduce the pluripotent stem cells remaining in an undifferentiated state when inducing the differentiation of a pluripotent stem cell population.

4 Claims, 10 Drawing Sheets

METHOD FOR REDUCING PLURIPOTENT STEM CELLS, METHOD FOR PRODUCING CELL POPULATION HAVING REDUCED PLURIPOTENT STEM CELLS

CROSS-REFERENCE TO RELATED APPLICATIONS

This application is a 371 National Phase application of PCT/JP2016/074545, filed Aug. 23, 2016, which application claims priority to Japanese Application no. JP 2015-171230, filed Aug. 31, 2015, the teaching both of which are hereby incorporated by reference in their entireties for all purposes.

TECHNICAL FIELD

The present invention relates to a method for reducing pluripotent stem cells. In addition, the present invention relates to a method for producing a cell population having reduced pluripotent stem cells.

BACKGROUND ART

There has been a growing level of activity in the development of therapeutic technology in recent years, and attempts at the clinical application thereof have been made at numerous institutions both in Japan and overseas. Various methods have been developed for this purpose, including methods consisting of the in vitro culturing of cells harvested from the body of a patient followed by re-transplanting the cells back into the patient, methods consisting of introducing a certain specific gene into harvested cells followed by returning the cells to the body, and transplantation methods consisting of seeding cells on a cell scaffold to construct three-dimensional structures. These technologies are used as medical technologies in the field of regenerative medicine, and have the potential to be able to treat diseases that were difficult to cure completely with conventional treatment. Consequently, the earliest possible practical application of effective cell-based therapeutic technologies is earnestly awaited so as to allow these technologies to be applied to numerous diseases.

Cells isolated from tissue or blood harvested from the body of a patient per se (autologous cells), cells isolated from tissue or blood harvested from the body of another person (heterologous cells), or established cells and the like are used in the field of regenerative medicine. The type of cell is suitably selected according to the disease site and pathology. Rejection reactions attributable to immunity present problems when transplanting cells. In the case cells different from one's own cells (heterologous cells) are transplanted, normally the type of major histocompatibility complex (MHC) does not match, resulting in the onset of a rejection reaction that prevents the cells from grafting.

On the other hand, in the case of using autologous cells, there is no occurrence of rejection reactions since the MHC types match by virtue of using the patient's own cells. Consequently, although regenerative medicine using autologous cells is preferable from the viewpoint of immunorejection, in the case of using autologous cells, since cells or tissue are harvested for each patient, the cells require treatment such as so-called "order-made" culturing resulting in exorbitant costs. On the other hand, treatment using heterologous cells would make it possible to ensure the required cells or tissues in advance and heterologous cells retained in storage could be used when a transplant was required, thereby making the use of heterologous cells preferable from the viewpoint of reducing costs. In this case, immunosuppressants can be used to avoid immunorejection in order to prevent the transplanted heterologous cells from being subjected to immunorejection within the body of the recipient.

Some of the cell types used in regenerative medicine either do not divide or grow or hardly grow at all in in vitro culture environments. Cardiomyocytes and nerve cells fall into this category, and it has been difficult to use such cells in regenerative medicine. However, with the discovery of pluripotent stem cells such as embryonic stem cells (ES cells) and induced pluripotent stem cells (iPS), even in the case of cells that do not divide or grow in the manner of cardiomyocytes and nerve cells, these cells have been able to be produced by inducing to differentiate from pluripotent stem cells, enabling these cells to be provided for use in regenerative medicine.

Pluripotent stem cells such as ES cells or iPS cells have the property of being able to differentiate into nearly all cells that compose the body. In addition, since ES cells or iPS cells, which retain the ability to remain undifferentiated prior to differentiation, have a self-replicating ability, they can basically be grown infinitely. Consequently, even in cases requiring large numbers of cells, pluripotent stem cells can theoretically be grown to the required number of cells. It has thus become possible to obtain the required number of cells by inducing pluripotent stem cells obtained in this manner to differentiate into any somatic cell.

Although ES cells and iPS cells can be grown in infinite numbers and can be induced to differentiate into any somatic cell, when cells still retaining the ability to remain undifferentiated are transplanted into the body, there is the risk of these cells forming a teratoma, which is a type of tumor, due to the pluripotency thereof. Although such problems do not occur if undifferentiated ES cells or iPS cells do not remain in populations of somatic cells that have been induced to differentiate from ES cells or iPS cells, if these ES cells or iPS cells that are still undifferentiated end up being transplanted into the body while remaining within a somatic cell population, there is the risk of the formation of a teratoma, thereby resulting concerns over safety (Non-Patent Document 1). Consequently, there is a need for a technology that reduces the number of undifferentiated pluripotent stem cells present in cell populations that have been induced to differentiate from pluripotent stem cells.

In order to overcome these problems, methods using a cell sorter (Non-Patent Document 2), methods incorporating suicide genes (Non-Patent Document 3) and methods using chemical inhibitors (Non-Patent Document 4, Non-Patent Document 5) were developed as methods for eliminating or reducing undifferentiated pluripotent stem cells from cell populations that underwent differentiation induction treatment. However, in the case of methods using a cell sorter, a large number of antibodies had to be used to recognize antigens present on the cell surface, thereby requiring considerable costs while also resulting in the problem of requiring a long period of time for treatment. In addition, methods incorporating suicide genes resulted in uncertainty regarding the safety of the cells incorporating such genes after transplant, thereby presenting problems in terms of clinical application. In addition, methods using chemical inhibitors had problems with efficiency and safety associated with the elimination or reduction of pluripotent stem cells.

PRIOR ART DOCUMENTS

Patent Documents

[Patent Document 1] International Publication No. WO 13/187359

Non-Patent Documents

[Non-Patent Document 1] Gropp, M., et al. (2012), Standardization of the teratoma assay for analysis of pluripotency of human ES cells and biosafety of their differentiated progeny, PLoS ONE 7, e45532.
[Non-Patent Document 2] Ben-David, U., et al. (2013), Immunologic and chemical targeting of the tight-junction protein Claudin-6 eliminates tumorigenic human pluripotent stem cells, Nat. Commun. 4, 1992.
[Non-Patent Document 3] Schuldiner, M., et al. (2003), Selective ablation of human embryonic stem cells expressing a "suicide" gene, Stem Cells 21, 257-265.
[Non-Patent Document 4] Ben-David, U., et al. (2013), Selective elimination of human pluripotent stem cells by an oleate synthesis inhibitor discovered in a high-throughput screen, Cell Stem Cell 12, 167-179.
[Non-Patent Document 5] Richards, M., et al. (2014), A new class of pluripotent stem cell cytotoxic small molecules, PLoS ONE 9, e85039.

DISCLOSURE OF THE INVENTION

Problems to be Solved by the Invention

An object of the present invention is to resolve the problems associated with eliminating or reducing pluripotent stem cells remaining when a pluripotent stem cell population has been induced to differentiate as described above. Namely, an object of the present invention is to provide a method for eliminating or reducing pluripotent stem cells and a method for producing a cell population from which pluripotent stem cells have been eliminated or reduced.

Means for Solving the Problems

The inventors of the present invention conducted extensive research and development in conjunction with studies from various perspectives in order to solve the aforementioned problems. As a result, it was surprisingly found that pluripotent stem cells can be induced to undergo apoptosis and die by an extremely simple and inexpensive method consisting of raising the culture temperature for a fixed period of time, and that conversely, pluripotent stem cells that have become somatic cells as a result of having been induced to differentiate are resistant to high temperatures. In addition, it was also found that undifferentiated pluripotent stem cells remaining after having induced a pluripotent stem cell population to differentiate can also be reduced by inducing apoptosis in the pluripotent stem cells in the same manner as when culturing at high temperatures by activating an agonist of a high temperature-sensitive TRP channel in the form of transient receptor potential vanilloid 1 (TRPV-1). Namely, the present invention is as indicated below.

[1] A method for culturing a cell population containing pluripotent stem cells and differentiated cells derived from pluripotent stem cells at a temperature of 40.5° C. or higher to reduce the pluripotent stem cells contained in the cell population.

[2] The method described in [1], wherein the temperature is 41° C. to 43° C.

[3] The method described in [1] or [2], wherein the duration of culturing at the temperature is within the range of 10 hours to 72 hours.

[4] The method described in any of [1] to [3], wherein the pluripotent stem cells are induced pluripotent stem cells and/or embryonic stem cells.

[5] The method described in any of [1] to [4], wherein the differentiated cells are cardiomyocytes, cardiomyoblasts, fibroblasts, parietal cells and/or vascular endothelial cells.

[6] A cell population obtained according to the method described in any of [1] to [5] in which the pluripotent stem cells have been reduced.

[7] A method for reducing pluripotent stem cells from a cell population containing pluripotent stem cells and differentiated cells derived from pluripotent stem cells that includes a step for activating TRPV-1 expressed in the pluripotent stem cells contained in the cell population.

[8] The method described in [7], wherein the step for activating TRPV-1 is a step for activating the TRPV-1 by culturing at a temperature of 40.5° C. or higher.

[9] The method described in [8], wherein the temperature is 40.5° C. to 45° C.

[10] The method described in [8] or [9], wherein the temperature is 41° C. to 43° C.

[11] The method described in any of [8] to [10], wherein the duration of the step for activating the TRPV-1 by culturing at the temperature is within the range of 10 hours to 72 hours.

[12] The method described in [7], wherein the step for activating TRPV-1 is a step for adding a TRPV-1 agonist.

[13] The method described in [12], wherein the agonist is one type or two or more types of agonists selected from the group consisting of capsaicin, N-oleoyldopamine (OLDA), arvanil, olvanil, AM404 (anandamide), 2-APB, NADA, PPAHV and anti-TRPV-1 antibody.

[14] The method described in any of [7] to [13], wherein the pluripotent stem cells are induced pluripotent stem cells and/or embryonic stem cells.

[15] The method described in any of [7] to [14], wherein the differentiated cells are cardiomyocytes, cardiomyoblasts, fibroblasts, parietal cells and/or vascular endothelial cells.

[16] A cell population obtained according to the method described in any of [7] to [15] in which the pluripotent stem cells have been reduced.

[17] A method for culturing a cell population containing pluripotent stem cells and differentiated cells derived from pluripotent stem cells in a medium to which has been added a TRPV-1 agonist to reduce the pluripotent stem cells contained in the cell population.

[18] The method described in [17], wherein the agonist is one type or two or more types of agonists selected from the group consisting of capsaicin, N-oleoyldopamine (OLDA), arvanil, olvanil, AM404 (anandamide), 2-APB, NADA, PPAHV and anti-TRPV-1 antibody.

[19] A cell population obtained according to the method described in [17] or [18] in which the pluripotent stem cells have been reduced.

[20] A method for producing a second cell population in which pluripotent stem cells have been reduced from a first cell population containing pluripotent stem cells and differentiated cells derived from pluripotent stem cells, including: a step for activating TRPV-1 expressed in the pluripotent stem cells contained in the first cell population.

[21] The method described in [20], wherein the step for activating TRPV-1 is a step for activating TRPV-1 by culturing at a temperature of 40.5° C. or higher.

[22] The method described in [20] or [21], wherein the temperature is 41° C. to 43° C.

[23] The method described in [20], wherein the step for activating TRPV-1 is a step for adding a TRPV-1 agonist.

[24] The method described in [23], wherein the agonist is one type or two or more types of agonists selected from the group consisting of capsaicin, N-oleoyldopamine (OLDA), arvanil, olvanil, AM404 (anandamide), 2-APB, NADA, PPAHV and anti-TRPV-1 antibody.

Effects of the Invention

According to the present invention, undifferentiated pluripotent stem cells can be easily eliminated or reduced from a cell population containing differentiated pluripotent stem cells, obtained by inducing pluripotent stem cells to differentiate, and residual pluripotent stem cells that have not been induced to differentiate.

In addition, a cell population obtained according thereto has a reduced proportion of undifferentiated pluripotent stem cells and a lower probability of forming a tumor when used as a graft.

BRIEF DESCRIPTION OF THE DRAWINGS

In FIG. 1A, human iPS cells cultured on laminin E8 fragments were cultured for 1 day or 2 days at 37° C., 40° C., 41° C. or 42° C. The upper panels indicate phase-contrast images and the bars represent 100 μm. The middle panels indicate Hoechst staining (blue) images and the bars represent 200 μm. The lower panels indicate montage images of 36 fields (6×6) of the Hoechst staining images. FIG. 1B is a graph indicating changes in the number of cells for each temperature condition (n=3). FIG. 1C depicts images indicating TUNEL-positive cells (green). The cell nuclei were stained with Hoechst stain (blue). FIG. 1D is a graph indicating the number of TUNEL-positive cells (n=3).

In FIG. 2A, human iPS cells cultured on laminin E8 fragments were cultured for 1 and 2 days at 37° C. or 42° C. The upper panels indicate phase-contrast images and the bars represent 100 μm. The middle panels indicate images obtained following Oct4 staining (green) and Hoechst staining (blue), and the bars represent 200 μm. The lower panels indicate montage images of 36 fields (6×6) following Oct4 staining. FIG. 2B is a graph indicating the number of Oct4-positive cells in 36 fields (6×6) (n=3).

In FIG. 1A, the upper panels indicate phase-contrast images and the bars represent 100 μm. The middle panels indicate Hoechst staining images (blue) and the bars represent 200 μm. The lower panels indicate montage images of 36 fields (6×6) of the Hoechst staining images. FIG. 3B is a graph indicating changes in the number of cells for each temperature condition. The number of cells indicates the total number of cells of 36 fields.

In FIG. 4A, human iPS cells cultured on MEF were cultured for 1 and 2 days at 42° C. The upper panels indicate phase-contrast images and the bars represent 100 μm. The middle panels indicate images obtained following Oct4 staining (green) and Hoechst staining (blue), and the bars represent 200 μm. The lower panels indicate montage images of 81 fields (9×9) of Oct4 staining images. FIG. 4B is a graph indicating the numbers of Oct4-positive cells in 81 fields at each time (n=3). FIG. 4C indicates the results of a co-culturing experiment using iPS cells and cardiomyocytes derived from iPS cells. Cell aggregates of the iPS cells and cells derived from iPS cells were cultured at 37° C. or 42° C. in AK03 medium or DMEM containing 10% FBS two days after the start of co-culturing. The top row of panels indicates phase-contrast images and the bars represent 100 μm. The third row of panels indicates Oct4 immunofluorescent images (green). The fourth row of panels indicates cTnT immunofluorescent images (red). The bottom row of panels indicates cell nuclei stained with Hoechst stain (blue). The bars represent 200 μm. The second row of panels indicates merged images of the Oct4 immunofluorescent images, cTnT immunofluorescent images and Hoechst immunofluorescent images. FIG. 4D is a graph indicating changes in the numbers of Oct4-positive cells in 36 fields.

FIG. 5A depicts images of cardiomyocytes. The first row of panels indicates merged images of Nkx2.5 (red), cTnT (green) and Hoechst (blue) immunofluorescent images. The second row of panels indicates montage images of 36 fields (6×6) of cTnT staining images. The third row of panels indicates Nkx2.5 staining images. The fourth row of panels indicates montage images of 36 fields (6×6) of Nks2.5 staining images. The bars represent 200 μm. FIG. 5B is a graph indicating the numbers of cTnT-positive cells and Nkx2.5-positive cells (n=2). FIG. 5C depicts images of fibroblasts. The first row of panels indicates phase-contrast images and the bars represent 100 μm. The second row of panels indicates vimentin (green) and Hoechst (blue) staining images. The third row of panels indicates montage images of 36 fields (6×6) of the vimentin staining images. The fourth row of panels indicates SM22 (red) and Hoechst (blue) staining images. The fifth row of panels indicates montage images of 36 fields (6×6) of the SM22 staining images. FIG. 5D depicts graphs indicating changes in the numbers of vimentin-positive cells and SM22-positive cells (n=4). *: $p<0.5$ vs. Day 0, **: $p<0.01$ vs. Day 0.

FIG. 6A depicts graphs indicating the expression levels of mRNA by human iPS cell-derived cardiomyocytes after inducing differentiation to heart muscle at each time during culturing at 42° C. (n=3). The Y axis indicates expression level as compared with GAPDH mRNA (*: $p<0.05$ vs. pre). FIG. 6B depicts graphs indicating expression levels of Lin28 and Oct4 mRNA by human iPS cell-derived cardiomyocytes following induction of differentiation to cardiac muscle at each time during culturing at 42° C. (n=3). The Y axis indicates the expression level as compared with GAPDH mRNA (*: $p<0.05$ vs. pre). FIG. 6C is a graph depicting the relative expression levels of Lin28 and Oct4 mRNA in iPS cell-derived cardiomyocytes (n=3). The graph indicates relative expression levels based on a value of 100% for the expression level of iPS cells. FIG. 6D depicts the effects of culturing at 42° C. on cell sheet fabrication. The drawing on the left indicates the culturing schedule. The drawing on the right indicates the status of the cell sheets.

FIG. 7A depicts graphs indicating the expression levels of TRPV-1 mRNA by feeder-less iPS cells (left graph, n=3) and iPS cell-derived cardiomyocytes (right graph, n=3). The Y axis indicates the relative expression level of TRPV-1 gene corrected with β-actin (*: p<0.05 vs. pre, *: p<0.01 vs. pre). FIG. 7B depicts graphs indicating expression levels of TRPV-1 mRNA by feeder-less iPS cells and iPS cell-derived cardiomyocytes before the start of culturing and after culturing for 24 hours at 42° C. (n=3). FIG. 7C depicts graphs indicating expression levels of TRPV-1 mRNA by iPS cells transfected with TRPV-1 siRNA or control siRNA (n=4). FIG. 7D indicates the results of culturing iPS cells transfected with TRPV-1 siRNA or control siRNA for 1 day at 37° C. or 42° C. The upper panels indicate phase-contrast images and the bars represent 100 μm. The middle panels indicate Hoechst staining images and the bars represent 200 μm. The lower images indicate montage images of 36 fields (6×6) of the Hoechst staining images. FIG. 7E depicts graphs indicating the number of cells under each temperature condition (n=3).

FIGS. 8A and 8B indicate the results of culturing iPS cells cultured on laminin E8 fragments following the addition of capsaicin. Vehicle-1 represents the control used in the experiment in which capsaicin was added at $2 \times 10^{-4}$ M, Vehicle-2 represents the control used in the experiment in which capsaicin was added at $1 \times 10^{-4}$ M, and Vehicle-3 represents the control used in the experiment in which capsaicin was added at $1 \times 10^{-5}$ M. The upper panels in FIG. 8A indicates phase-contrast images and the bars represent 100 μm. The middle panels indicate Hoechst staining images and the bars represent 200 μm. The lower panels indicate montage images of 36 fields (6×6) of the Hoechst staining images. FIG. 8B is a graph indicating the numbers of cells in 36 fields under each condition. FIGS. 8C and 8D indicate Nkx2.5-positive cells cultured by adding capsaicin to iPS cells cultured on laminin E8 fragments. Vehicle-1 represents the control used in the experiment in which capsaicin was added at $2 \times 10^{-4}$ M, and Vehicle-2 represents the control used in the experiment in which capsaicin was added at $1 \times 10^{-4}$ M. The upper panels of FIG. 8C indicate phase-contrast images and the bars represent 100 μm. The lower panels indicate merged images of Hoechst staining images (blue) and Hix2.5 staining images (green), and the bars represent 200 μm. FIG. 8D is a graph indicating the numbers of cells in 36 fields under each condition.

FIGS. 9A and 9B indicate the results of culturing iPS cells cultured on laminin E8 fragments following the addition of OLDA. The upper panels of FIG. 9A indicate phase-contrast images and the bars represent 100 μm. The middle panels indicate Hoechst staining images (blue) and the bars represent 200 μm. The lower panels indicate montage images of 36 fields (6×6) of the Hoechst staining images. FIG. 9B is a graph indicating the numbers of cells in 36 fields under each condition (n=3). FIGS. 9C and 9D indicate the results of culturing iPS cell-derived cardiomyocytes following the addition of OLDA. The upper panels of FIG. 9C indicate merged images of cTnT staining images (green), Nkx2.5 staining images (red) and Hoechst staining images (blue), and the bars represent 200 μm. The middle panels indicate montage images of 36 fields (6×6) of cTnT staining images. The lower panels indicate montage images of 36 fields (6×6) of Hkx2.5 staining images. FIG. 9D depicts graphs indicating the number of cTnT-positive cells and Nkx2.5-positive cells (in 36 fields) after culturing iPS cell-derived cardiomyocytes following the addition of OLDA. FIG. 9E is a graph indicating the expression levels of Lin28 mRNA after culturing iPS cell-derived cardiomyocytes for 2 days at 42° C. or after culturing for 2 days at 37° C. in the presence of OLDA (5 μM). The Y axis indicates the relative expression levels of Lin28 by iPS cell-derived cardiomyocytes versus undifferentiated iPS cells cultured on MEF.

FIGS. 10A and 10B indicate the results of culturing for 1 day by adding arvanil to iPS cells cultured on laminin E8 fragments. The upper panels of FIG. 10A indicate phase-contrast images and the bars represent 100 μm. The middle panels indicate Hoechst staining images (blue) and the bars represent 200 μm. The lower panels indicate montage images of 36 fields (6×6) of the Hoechst staining images. FIG. 10B is a graph indicating the numbers of cells in 36 fields under the condition of culturing following the addition of arvanil (n=3).

MODE FOR CARRYING OUT THE INVENTION

Figure 1:
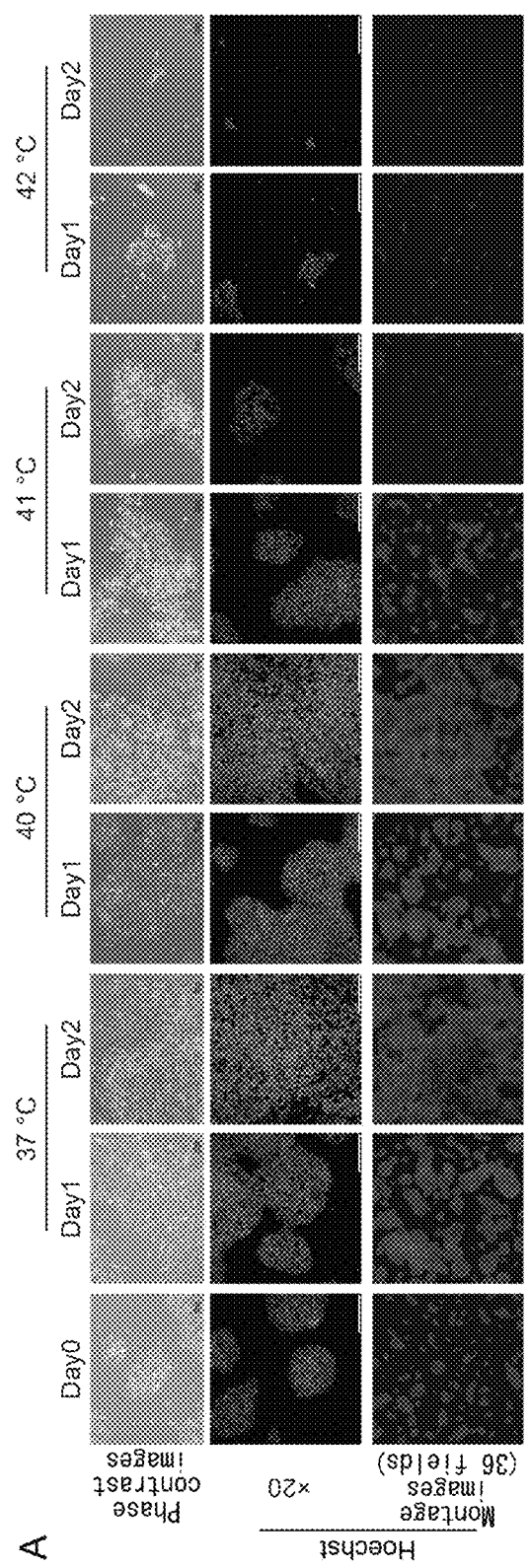
FIG. 1 illustrates the effects of culture temperature on iPS cells cultured under feeder-less conditions.
Figure 1:
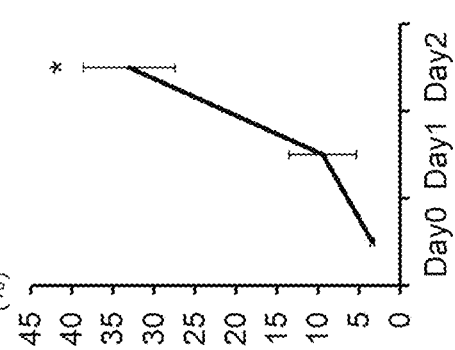
Figure 1:
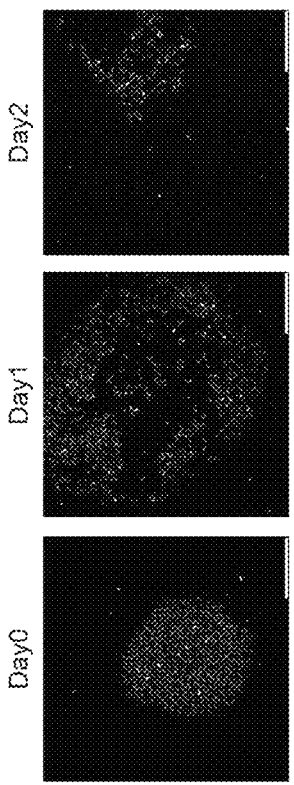
Figure 1:
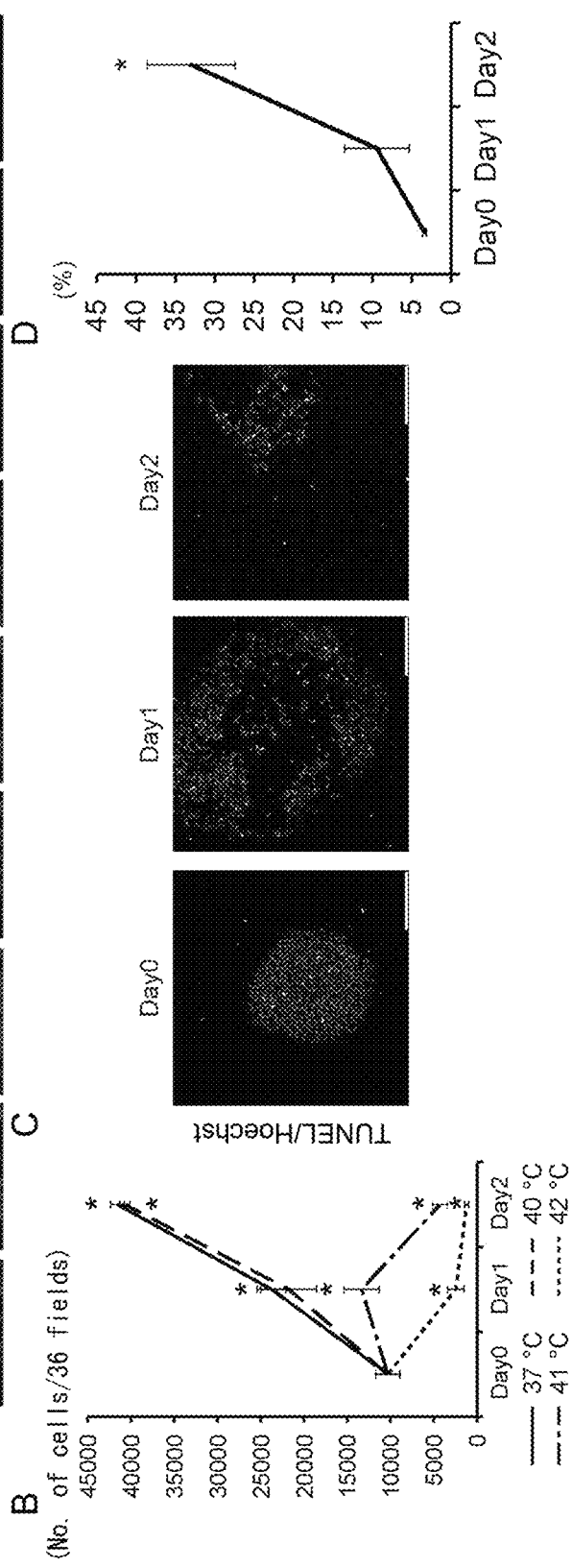

The present invention relates to a method for eliminating or reducing pluripotent stem cells and a method for producing a cell population in which pluripotent stem cells have been eliminated or reduced. In the present invention, pluripotent stem cells refer to cells having the ability to self-replicate and differentiate by having the ability to form all types of cells that compose the body (pluripotent cells). The ability to self-replicate refers to the ability to create two undifferentiated cells identical to itself from a single cell. Examples of pluripotent stem cells used in the present invention include embryonic stem cells (ES cells), embryonic carcinoma cells (EC cells), trophoblast stem cells (TS cells), epiblast stem cells (EpiS cells), embryonic germ cells (EG cells), multipotent germline stem cells (mGS cells), and induced pluripotent stem cells (iPS cells).

The pluripotent stem cells used in the present invention can be defined as cells that (1) have alkaline phosphatase activity in the undifferentiated state, and/or (2) express transcription factor Oct3/4 (also referred to as Oct3, Oct4), Nanog or Sox2, and/or (3) express proteins of stage-specific embryonic antigens (SSEA)-3, SSEA-4, Tra-1 60, Tra-1 81 or Lin 28, and/or (4) have the ability to differentiate into tissue derived from the three germ layers of the endoderm, mesoderm and ectoderm. Whether or not a pluripotent stem cell has the ability to differentiate into tissue derived from the three germ layers can be determined by transplanting the target cells beneath the skin of a mouse or other suitable test animal and evaluating whether or not the cells have the ability to form a teratoma.

The pluripotent stem cells used in the present invention are preferably cells that have been preliminarily confirmed to be stocked as cells that satisfy the aforementioned definitions such as cells (cell populations) distributed by cell banks operated by public institutions (such as the Kyoto University Center for iPS Cell Research or RIKEN) or private institutions (such as iPS Academia Japan, Inc.), and in this case, the proportion of pluripotent stems cells contained in a cell population can be easily confirmed by simply confirming whether or not the gene expression level and/or protein expression level of at least one pluripotency marker among pluripotency markers such as alkaline phosphatase, Nanog, Sox2, Oct3/4, Tra-1 60, Tra-1 81, SSEA-3, SSEA-4 and Lin28 is high in comparison with non-pluripotent stem cells. In the present invention, the method used to measure a pluripotency marker of pluripotent stem cells may be in accordance with established methods, and examples of techniques that can be used include RT-PCR, measurement methods using a flow cytometer, measurement methods using western blotting, measurement methods using immunohistochemical staining, and methods using a microarray.

The pluripotent stem cells used in the present invention may be differentiated pluripotent stem cells, such as pluripotent stem cells obtained by reprogramming somatic cells. Examples of methods used to reprogram somatic cells include, but are not limited to, methods consisting of removing the nuclei of unfertilized eggs and transplanting the nuclei of somatic cells, methods consisting of fusing somatic cells and ES cells, and methods consisting of reprogramming cells by introducing a specific reprogramming factor (such as Oct3/4, Nanog, Sox2, c-Myc, L-Myc, Lin28 or Klf4) into somatic cells. There are no particular limitations on the method used to introduce a reprogramming factor into cells, and for example, methods using a virus vector, methods using a plasmid vector, methods introducing a reprogramming factor in the form of mRNA or methods introducing a reprogramming factor in the form of a protein may be used.

In embodiments of the present invention, although non-pluripotent stem cells refer to cells that do not satisfy the aforementioned definition of pluripotent stem cells, more specifically, these refer to differentiated somatic cells composing body tissue that have lost the ability to differentiate into any of the germ layers of the endoderm, mesoderm or ectoderm. Examples thereof include cells that compose the body, such as cardiomyocytes, myoblasts, mesenchymal stem cells, vascular endothelial cells, vascular endothelial progenitor cells, fibroblasts, bone marrow-derived cells, fat-derived cells, liver parenchymal cells, sinusoidal endothelial cells, Kupffer cells, stellate cells, pit cells, biliary epithelial cells, renal cells, granule cells, collecting duct epithelial cells, parietal epithelial cells, podocytes, mesangial cells, smooth muscle cells, tubule cells, intercalated cells, glomerular cells, adrenomedullary cells, adrenocortical cells, glomerulosa cells, fasciculata cells, reticulata cells, epidermal keratinocytes, melanocytes, arrector pili muscle cells, hair follicle cells, buccal mucosal cells, gastric mucosal cells, intestinal mucosal cells, olfactory epithelial cells, oral mucosal cells, endometrial cells, midbrain dopamine neurons, cerebral neurons, retinal cells, cerebellar neurons, hypothalamic endocrine cells, T cells, B cells, neutrophils, eosinophils, basophils or monocytes, as well as multipotent somatic stem cells having the ability to form cell types of a single line. Somatic cells do not include reproductive cells.

There are no particular limitations on the origin of the animal species of the cells used in the present invention, and examples thereof include mammals such as humans, rats, mice, guinea pigs, marmosets, rabbits, dogs, cats, sheep, pigs, goats, monkeys, chimpanzees or immunodeficient varieties thereof, birds, reptiles, amphibians, fish and insects. Cells derived from humans are preferably used in the case of using cells obtained according to the present invention to treat humans, cells derived from pigs are preferably used in the case of using to treat pigs, cells derived from monkeys are preferably used in the case of using to treat monkeys, and cells derived from chimpanzees are preferably used in the case of using to treat chimpanzees. In addition, in the case the target of treatment is a human, the cells may be cells harvested from the patient per se (autologous cells), cells harvested from the cells of another person (heterologous cells), or a commercially available cell line may be used.

In the present invention, there are no particular limitations on the non-pluripotent stem cells obtained by inducing differentiation from pluripotent stem cells. For example, in the case of using for the purpose of regenerating myocardial tissue or evaluating myocardial function, examples include one type, or a mixture of two or more types, of cardiomyocytes, cardiomyoblasts, myoblasts, mesenchymal stem cells, vascular endothelial cells vascular endothelial progenitor cells, fibroblasts, bone marrow-derived cells and fat-derived cells. In the case of using for the purpose of regenerating liver tissue, fabricating an artificial liver that mimics liver tissue, or evaluating liver function, examples of cells obtained by inducing differentiation from pluripotent stem cells include one type, or a mixture of two or more types, of liver parenchymal cells, sinusoidal endothelial cells, Kupffer cells, stellate cells, pit cells, biliary epithelial cells, vascular endothelial cells, vascular endothelial progenitor cells, fibroblasts, bone marrow-derived cells, fat-derived cells and mesenchymal cells. In the case of using for the purpose of regenerating renal tissue, fabricating an artificial kidney that mimics renal tissue or evaluating renal function, examples of cells obtained by inducing differentiation from pluripotent stem cells include one type, or a mixture of two or more types of, renal cells, granule cells, collecting duct epithelial cells, parietal epithelial cells, podocytes, mesangial cells, smooth muscle cells, tubule cells, intercalated cells, glomerular cells, vascular endothelial cells, vascular endothelial progenitor cells, fibroblasts, bone marrow-derived cells, fat-derived cells and mesenchymal stem cells. In the case of using for the purpose of regenerating adrenal tissue, fabricating an artificial adrenal gland that mimics the adrenal gland, or evaluating adrenal function, examples of cells used include one type, or a mixture of two or more types, of adrenomedullary cells, adrenocortical cells, glomerulosa cells, fasciculata cells, reticulata cells, vascular endothelial cells, vascular endothelial progenitor cells, fibroblasts, bone marrow-derived cells, fat-derived cells and mesenchymal stem cells. In the case of using for the purpose of regenerating skin or evaluating skin function, examples of cells obtained by inducing differentiation from pluripotent stem cells include one type, or a mixture of two or more types, of epidermal keratinocytes, melanocytes, arrector pili muscle cells, hair follicle cells, vascular endothelial cells, vascular endothelial progenitor cells, fibroblasts, bone marrow-derived cells, fat-derived cells and mesenchymal stem cells. In the case of using for the purpose of regenerating mucosal tissue or evaluating mucosal tissue function, examples of cells obtained by inducing differentiation from pluripotent stem cells include one type, or a mixture of two or more types, of buccal mucosal cells, gastric mucosal cells, intestinal mucosal cells, olfactory epithelial cells, oral mucosal cells and endometrial cells. In the case of using for the purpose of regenerating neural tissue or evaluating neural function, examples of cells obtained by inducing differentiation from pluripotent stem cells include, but are not limited to, one type, or a mixture of two or more types, of midbrain dopamine neurons, cerebral neurons, retinal cells, cerebellar neurons and hypothalamic endocrine cells. In the case of using for the purpose of obtaining cells that compose the blood, examples of cell obtained by inducing differentiation from pluripotent stem cells include, but are not limited to, one type, or a mixture of two or more types, of T cells, B cells, neutrophils, eosinophils, basophils or monocytes, platelets and erythrocytes.

In the present description, a "medium" refers to a cell culture medium for culturing cells, and particularly animal cells. The term "medium" is used in the same context as a cell culture broth. Consequently, a medium used in the present invention refers to a liquid medium. A routinely used medium can be used for the type of medium, and is suitably determined according to the type of cells to be cultured.

In the present invention, there are no particular limitations on the culture method for maintaining pluripotent stem cells in an undifferentiated state prior to inducing differentiation, and may be in accordance with an established method. In addition, there are also no particular limitations on the method used to induce differentiation of pluripotent stem cells, and a method for inducing differentiation is used that has been optimized for obtaining the target cells. There are also no particular limitations on the culture method for maintaining pluripotent stem cells in an undifferentiated state or culturing for inducing differentiation, and may be carried out in a flat culture dish or by suspension stirring three-dimensional culturing.

In the present invention, "reducing" pluripotent stem cells refers to reducing the relative number of pluripotent stem cells in a cell population by completely or partially eliminating or completely or partially killing off target pluripotent stem cells from a cell population containing pluripotent stem cells and differentiated cells derived from pluripotent stem cells (also referred to as a "first cell population"), or interrupting or delaying the growth of target pluripotent stem cells. Reduction of pluripotent stem cells in the present invention is brought about by reducing the relative number of pluripotent stem cells in a cell population by inducing apoptosis or necrosis or by interrupting or delaying only the cell cycle of the pluripotent stem cells. In the present invention, "reducing" pluripotent stem cells refers to reducing, for example, 5%, 10%, 15%, 20%, 25%, 30%, 35%, 40%, 45%, 50%, 55%, 60%, 65%, 70%, 75%, 80%, 85%, 90%, 95%, 99% or 100% of the pluripotent stem cells in comparison with the case of culturing the cell population containing pluripotent stem cells by a conventional culturing method instead of using the method of the present invention. In the present description, a cell population obtained by reducing pluripotent stem cells from a cell population containing pluripotent stem cells and differentiated cells derived from pluripotent stem cells (first cell population) according to the method of the present invention is also referred to as a "second cell population".

Pluripotent stem cells and differentiated cells induced to differentiate from pluripotent stem cells have conventionally been cultured at the body temperature of warm-blooded animals of about 37°. In the present invention, pluripotent stem cells can be eliminated or reduced by culturing at a temperature higher than body temperature. In the present invention, the culture temperature for eliminating or reducing pluripotent stem cells is 40.5° C. or higher, such as a temperature of 40.5° C., 40.6° C., 40.7° C., 40.8° C., 40.9° C., 41.0° C., 40.1° C., 40.2° C., 40.3° C., 40.4° C., 40.5° C., 40.6° C., 40.7° C., 40.8° C., 40.9° C., 41.0° C., 41.1° C., 41.2° C., 41.3° C., 41.4° C., 41.5° C., 41.6° C., 41.7° C., 41.8° C., 41.9° C., 42.0° C., 42.1° C., 42.2° C., 42.3° C., 42.4° C., 42.5° C., 42.6° C., 42.7° C., 42.8° C., 42.9° C., 43.0° C., 43.1° C., 43.2° C., 43.3° C., 43.4° C., 43.5° C., 43.6° C., 43.7° C., 43.8° C., 43.9° C., 44.0° C., 44.1° C., 44.2° C., 44.3° C., 44.4° C., 44.5° C., 44.6° C., 44.7° C., 44.8° C., 44.9° C. or 45.0° C. In addition, the culture temperature for eliminating or reducing pluripotent stem cells may be 40.5° C. to 45.0° C., 40.7° C. to 43.7° C., 40.8° C. to 43.5° C., 40.7° C. to 43.7° C., 40.8° C. to 43.5° C., 40.9° C. to 43.3° C. or 41.0° C. to 43.0° C. In particular, culturing within a temperature range of 41.0° C. to 43.0° C. is preferable since the growth of pluripotent stem cells is interrupted and differentiated cells are subjected to hardly any damage after having induced the pluripotent stem cells to differentiate. In the present invention, a step for culturing a cell population containing pluripotent stem cells and differentiated cells derived from pluripotent stem cells at a temperature of 40.5° C. or more may be that which reduces pluripotent stem cells by activating TRPV-1 to be subsequently described, or may be that which reduces pluripotent stem cells by an action other than activating TRPV-1.

In the present invention, although the duration of culturing at a temperature higher than body temperature in order to eliminate or reduce pluripotent stem cells is suitably selected according to the culture temperature, the duration of culturing may be, for example, 6 hours, 7 hours, 8, hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 73 hours, 74 hours, 75 hours, 76 hours, 77 hours, 78 hours, 79 hours or 80 hours. In addition, the duration of culturing may be 6 hours to 80 hours, 9 hours to 75 hours, 10 hours to 72 hours, 11 hours to 70 hours or 12 hours to 68 hours. For example, in the case of culturing at 41.0° C. to 43.0° C., culturing for a duration within the range of 10 hours to 72 hours reduces the growth of pluripotent stem cells and inhibits cytotoxic activity on the differentiated cells after the pluripotent stem cells have been induced to differentiate, thereby making this preferable.

In the present invention, evaluation of residual pluripotent stem cells following induction of differentiation is in accordance with an established method, and there are no particular limitations thereon provided the residual pluripotent stem cells are evaluated by using expression of, for example, Oct4 (also referred to as Oct3 or Oct3/4), Lin28, SSEA-3, SSEA-4, Tra-1 60 or Tra-1 81, as an indicator. Examples of evaluation methods include confirmation by flow cytometry, confirmation of protein expression by western blotting and confirmation of the expression level of mRNA using real-time PCR, and there are no particular limitations thereon. In addition, evaluation of the proportion of somatic cells contained after having induced differentiation may be in accordance with an established method. For example, in the case of evaluating the proportion of cardiomyocytes, the proportion of cells expressing a protein or gene expressed in cells that compose the heart, such as cardiac troponin T (cTnT) or Nkx2.5, is evaluated. For example, in the case of evaluating the proportion of fibroblasts, the proportion of cells expressing a protein or gene expressed in fibroblasts, such as vimentin or SM22, is evaluated. In the case of evaluating the proportion of other somatic cells contained, the proportion of cells expressing a protein or gene specifically expressed by the target cells is evaluated, and there are no particular limitations thereon.

In the present invention, TRPV-1 (transient receptor potential cation channel subfamily V, member 1) refers to a membrane protein cloned as a capsaicin receptor. TRPV-1 is known as a non-selective cation channel that is activated in response to a wide range of intrinsic and extrinsic physical and chemical stimuli. TRPV-1 is activated at temperatures higher than 43° C. and is also activated by substances such as capsaicin or allyl isocyanates. When TRPV-1 is activated, cations flow into cells and an action potential is generated from activation of voltage-gated channels following neuron depolarization resulting in the induction of pain. In addition, TRPV-1 is also activated by low pH. Although TRPV-1 is mainly expressed in the sensory nervous system, it is also expressed in the central nervous system and other tissues, and is considered to be a molecule involved in the regulation and transmission of pain stimuli.

The present invention relates to a method for eliminating or reducing pluripotent stem cells from a cell population containing pluripotent stem cells and differentiated cells derived from pluripotent stem cells by activating TRPV-1 based on the finding that there are differences in the sensitivity to temperature and chemical substances of TRPV-1 between pluripotent stem cells and differentiated cells derived from pluripotent stem cells. Although examples of TRPV-1 agonists include capsaicin, N-oleoyldopamine (OLDA), arvanil, olvanil, AM404 (anandamide), 2-APB, NADA, PPAHV and anti-TRPV-1 antibody, in the present invention, there are no particular limitations thereon provided the agonist binds to TRPV-1 and demonstrates antagonistic activity thereon. In the present invention, the concentration of capsaicin may be 20 µM to 100 mM, 30 µM to 50 mM, 40 µM to 20 mM or 50 µM to 10 mM. In the present invention, the concentration of OLDA may be 600 nM to 100 mM, 750 nM to 10 mM, 1 µM to 1 mM or 2 µM to 750 µM. In the present invention, the concentration of arvanil may be 7 µg/mL (0.016 mM) to 10 mg/mL (22.746 mM), 10 µg/mL (0.023 mM) to 5 mg/mL (11.373 mM) or 15 µg/mL (0.034 mM) to 3 mg/mL (6.824 mM).

In the present invention, the method used to eliminate or remove pluripotent stem cells from a cell population containing pluripotent stem cells and differentiated cells derived from pluripotent stem cells after having been induced to differentiate may be carried out on a cell population after having subjected to treatment for inducing differentiation or may be carried out on cells or tissue after having undergone processing by tissue engineering such as by processing into a cell sheet, and is suitably selected according to the objective. In addition, the aforementioned method may also be used in combination with a convention method for eliminating or reducing pluripotent stem cells, and there are no particular limitations thereon. In addition, the aforementioned method may also use a method that allows the aforementioned TRPV-1 agonist to act while treating at a temperature that does not cause differentiated cells derived from pluripotent stem cells to die out.

In the present invention, a cell population includes components other than cells and there are no particular limitations thereon. Examples thereof include cell populations containing cells, and substances that compose extracellular matrix, such as collagen, proteoglycan, laminin, laminin 5, fibronectin, hyaluronic acid, entactin, tenascin or elastin, compositions containing cells, and extracellular matrix produced by cells. In addition, proteins that compose extracellular matrix may be gene-recombinant proteins or proteins produced from cells having a gene encoding that protein incorporated therein or cells introduced with a gene through the use of a vector and the like. In addition, the form of the cell population may be that obtained by laminating a plurality of layered cells (such as in the form of a cell sheet) or that obtained by suspending cells in a gel containing extracellular matrix followed by pouring into a mold.

A cell sheet in the present invention refers to a group of cells cultured using cell culture substrate composed of a single layer or a plurality of sheet-like cell layers obtained by detaching from the culture substrate. Although there are no particular limitations on the method used to obtain the cell sheet, examples thereof include a method consisting of culturing cells on cell culture substrate coated with a polymer that undergoes a change in the molecular structure thereof in response to a stimulus such as temperature, pH or light, followed by detaching the cells from the surface of the cell culture substrate in the form of a sheet as a result of changing the surface of the cell culture substrate by changing temperature, pH, light or other conditions, and a method consisting of culturing cells with arbitrary cell culture substrate followed by physically detaching the cells from the edges of the cell culture substrate with a forceps and the like. A particularly preferable method consists of culturing cells on a cell culture support having a polymer, which undergoes a change in hydration force over a temperature range of 0° C. to 80° C., coated on the surface thereof, at a temperature at which the hydration force of the polymer is weak, followed by culturing while causing the medium to change to a temperature at which the hydration force of the polymer becomes stronger to detach the cells in the form of a sheet. At that time, the cells are cultured on a cell culture support having a polymer, which undergoes a change in hydration force over a temperature range of 0° C. to 80° C., coated on the surface thereof at a temperature at which the hydration force of the polymer is weak. Normally that temperature is preferably a temperature of 37° C., the temperature at which the cells are cultured. The temperature-responsive polymer used in the present invention may be a homopolymer or copolymer. An example thereof is described in Japanese Unexamined Patent Publication No. H2-211865.

Some cell types have difficulty in adhering to cell culture substrate, and in such cases, the cells may be cultured by coating the cell culture substrate with, for example, collagen, laminin, laminin 5, fibronectin or Matrigel either alone or as a mixture of two or more types thereof. These cell adhesive proteins may be coated in accordance with ordinary methods, and for example, an aqueous solution of a cell adhesive protein is normally coated onto the surface of the substrate followed by removing the aqueous solution and rinsing.

In the method of the present invention, although the number of cells seeded in order to fabricate a cell sheet varies according to the animal species of the cells used and the type of cells, the number of cells is typically $0.3 \times 10^4$ cells/cm$^2$ to $10 \times 10^6$ cells/cm$^2$, preferably $0.5 \times 10^4$ cells/cm$^2$ to $8 \times 10^6$ cells/cm$^2$, and more preferably $0.7 \times 10^4$ cells/cm$^2$ to $5 \times 10^6$ cells/cm$^2$. In the present invention, the cell sheet can be detached and recovered from the temperature-responsive culture substrate by making the temperature of the culture substrate to which the cultured cells are adhered to be equal to or higher than the upper limit critical solution temperature or equal to or lower than the lower limit critical solution temperature of the coated polymer. At that time, the temperature can be set in the medium or in another isotonic solution, and can be selected according to the objective. A method consisting of gently tapping or shaking the cell apparatus, a method consisting of agitating the medium using a pipette, or a method that uses a forceps may be used alone or in combination for the purpose of more rapidly and efficiently recovering the cells. There are no particular limitations on culture conditions other than temperature and may be in accordance with ordinary methods. For example, with respect to the medium used, a medium containing a known serum such as fetal bovine serum (FBS) may be used or a serum-free medium, to which serum has not been added, may be used.

A cardiomyocyte sheet using cardiomyocytes derived from pluripotent stem cells used in the present invention may contain non-cardiomyocytes, such as fibroblasts, parietal cells or vascular endothelial cells, induced to differentiate from pluripotent stem cells, in addition to the cardiomyocytes. Unnecessary cells can be removed, or conversely required cells can be added, using a cell sorter or antibody according to the objective. A "cardiomyocyte sheet" as described in examples in the present description contains, in addition to cardiomyocytes, cells induced to differentiate from pluripotent stem cells, such as fibroblasts, parietal cells, vascular endothelial cells or non-cardiomyocytes.

The following provides an explanation of the above matters using poly(N-isopropylacrylamide) as an example of a temperature-responsive polymer. Poly(N-isopropylacrylamide) is known to be a polymer that has a lower limit critical solution temperature of 31° C. and undergoes dehydration in water at a temperature of 31° C. or higher when in the free state, causing the polymer chain to aggregate and become cloudy. Conversely, the polymer chain is hydrated and becomes soluble in water at a temperature of 31° C. or lower. In the present invention, this polymer is coated and immobilized on the surface of culture substrate. Thus, although the polymer on the surface of the culture substrate is dehydrated in the same manner at a temperature of 31° C. or higher, since the polymer chain is coated and immobilized on the surface of the culture substrate, the surface of the culture substrate demonstrates hydrophobicity. Conversely, although the polymer on the surface of the culture substrate is hydrated at a temperature of 31° C. or lower, since the polymer chain is adhered and immobilized on the surface of the culture substrate, the surface of the culture substrate demonstrates hydrophilicity. The hydrophobic surface at this time is a suitable surface enabling adhesion and growth of cells, while the hydrophilic surface is a surface that prevents cells from adhering thereto, enabling cells during culturing or a cell sheet to be separated simply by cooling.

There are no particular limitations on the form of the cell culture substrate used to fabricate a cell sheet, and examples thereof include those in the form of a dish, multi-plate, flask or cell insert cultured on a porous membrane, and those in the form of a flat film. In the case the cultured cells are epithelial cells, the use of a cell insert enables the medium to make contact above and below the cells and the cells become layered, thereby making this preferable. Examples of the materials of coated cell culture substrate include glass, modified glass and compounds such as polystyrene or polymethyl methacrylate that are normally used to culture cells, as well as substances typically able to be shaped, such as polymer compounds other than those listed above, and ceramics.

The cell sheet in the present invention is not damaged by proteases such as dispase or trypsin during culturing. Consequently, the cell sheet detached from cell culture substrate retains adhesive proteins and the desmosome structure between cells is retained when cells are detached in the form of a sheet. As a result, in the case of affixing a cell sheet to an affected area of the body or laminating cell sheets, the cell sheet can be adhered resulting in the cell sheet taking efficiently to the body. With respect to the protease, dispase, although it is generally known that cell layers can be detached in a state in which 10% to 40% of the intercellular desmosome structure is retained, since nearly all of the basement membrane-like proteins between the cells and culture substrate are destroyed, the resulting cell sheet has a low level of strength. In contrast, the cell sheet of the present invention retains 60% or more of both desmosome structures and basement membrane-like proteins, thereby enabling various effects like those previously described to be obtained.

Although there are no particular limitations on the method used to fabricate a cell composition having a plurality of cell layers in the present invention, examples thereof include a method consisting of seeding cells in cell culture substrate and coating the cells with a gel containing a protein that composes extracellular matrix protein (such as laminin, collagen, gelatin, cadherin, hyaluronic acid, fibronectin, fibrin, elastin, chitin, chitosan or hydronectin), followed by further seeding cells to layer the cells thereon and obtain a cell composition having cell layers, and a method consisting of detaching cultured cells in the form of a sheet and laminating the cultured cell sheets using a cultured cell transfer tool as necessary. At that time, there are no particular limitations on the temperature of the medium provided that, in the case the aforementioned polymer coated on the cell culture substrate has an upper limit critical solution temperature, the temperature of the medium is equal to or lower than that temperature, while in the case the aforementioned polymer has a lower limit critical solution temperature, the temperature of the medium is equal to or higher than that temperature. However, it goes without saying that culturing at a low temperature that prevents cell growth (such as a temperature of 10° C. or lower) or culturing at a high temperature that causes the cultured cells to die (such as a temperature of 50° C. or higher) is unsuitable. There are no particular limitations on culturing conditions other than temperature and may be in accordance with ordinary methods. For example, the medium used may be medium to which a known serum such as fetal bovine serum (FBS) has been added or serum-free medium to which serum has not been added. In addition, a tool may be used to transfer the cell sheet as necessary. There are no particular limitations on the material or form of such tools provided they are able to grasp a detached cell sheet, and materials such as polyvinylidene difluoride (PVDF), silicon, polyvinyl alcohol, urethane, cellulose and derivatives thereof, chitin, chitosan, collagen, gelatin or fibrin glue are normally used while contacting the cell sheet in the form of a film, porous film, nonwoven fabric or woven fabric.

EXAMPLES

Although the following provides a more detailed explanation of the present invention based on examples thereof, the present invention is not limited by these examples.

(Antibodies)

Antibodies used in immunocytochemistry and flow cytometry in the examples are as indicated below.

Anti-cardiac troponin T (cTnT, Thermo Fisher Scientific Inc., Rockford, Ill., USA)

Anti-Tra-1 60 mouse monoclonal antibody (Millipore Corp., Billerica Mass., USA)

Anti-SM22 rabbit polyclonal antibody (Abcam plc, Cambridge, UK)

Anti-cardiac troponin T rabbit polyclonal antibody (Abcam plc, Cambridge, UK)

Anti-Nkx2.5 goat polyclonal antibody (Santa Cruz Biotechnology Inc., Santa Cruz, Calif., USA)

Anti-Oct4 goat polyclonal antibody (R&D Systems, Inc.)

Secondary antibodies were purchased from Jackson Immunoresearch Laboratories, Inc. (West Grove, Pa., USA). Reagents were purchased from Life Technologies Corp. (California, USA) unless specifically indicated otherwise.

(Culturing of Human iPS Cells)

Human iPS cell lines 253G1 and 2017 were purchased from RIKEN (Ibaraki, Japan). Transfer of human iPS cell line 1231A3 was received from Kyoto University. In experiments using feeder cells, iPS cells were placed on mouse embryonic fibroblasts (MEF) (Reprocell Inc., Tokyo) treated with mitomycin C followed by carrying out maintenance culturing under conditions of a humidified atmosphere at 5% $CO_2$ and 37° C. using primate ES/iPS cell medium (Reprocell Inc., Japan) containing 5 ng/mL of basic fibroblast growth factor (bFGF, Reprocell Inc., Japan). The iPS cells were subcultured every 3 to 4 days as small cell aggregates using ES/iPS cell dissociation solution (CTK solution, Reprocell Inc., Japan). In experiments not using feeder cells, the iPS cells were conditioned by culturing on iMatrix 511 (Nippi, Inc., Tokyo, Japan) using Stem Fit AK03 (Ajinomoto Corp., Tokyo, Japan) for the medium followed by maintenance culturing. The iPS cells were subcultured every 7 to 8 days as single cells using TrypLE Select (Life Technologies Corp., California, USA) (reference: Nakagawa, M., et al., A novel efficient feeder-free culture system for the derivation of human induced pluripotent stem cells, Sci. Rep., 2014; 4: 3594). Depending on the experiment, the iPS cells were cultured in an atmosphere at 5% $CO_2$ incubated at 40° C., 41° C. or 42° C. Samples were photographed and analyzed with an inverted microscope (Nikon Corp., Tokyo, Japan) and NIS-Elements software (Nikon Corp., Tokyo, Japan).

(Preparation of Human iPS Cells Expressing α-MHC Promoter and Rex-iPromoter-Induced Drug Resistance Genes)

Lentivirus vector containing both mouse α-myosin heavy chain (α-MHC) promoter-controlled puromycin resistance gene and rex-1 promoter-controlled neomycin resistance gene (α-MHC-puro rex-1-neo) was purchased from Addgene Inc. (Cambridge, Mass., USA). Use of this lentivirus vector makes it possible to screen for undifferentiated iPS cells only using G418 when growing human iPS cells, and screen for cardiomyocytes that have been induced to differentiate using puromycin following induction of differentiation to cardiac muscle. Gene-recombinant iPS cells were obtained according to the procedure described below.

(i) Preparation of Recombinant Lentivirus Vector

Vector gene introduction was carried out with Lipofectamine 2000 provided by a commercially available gene transfer kit, and preparation of recombinant lentivirus vector was carried out using ViraPower™ Lentivirus Packaging Mix (Invitrogen Corp.).

$5 \times 10^4$ cells/cm$^2$ of HEK293FT cells were seeded into 100 mm polystyrene culture dishes (Becton Dickinson and Company, Franklin Lakes, N.J., USA). After culturing for 24 hours, the vector (3 μg/culture dish) was introduced into the genes using the Transfectamine 2000 kit and OPTI-MEM (Invitrogen Corp.) followed by culturing for 8 hours at 37° C. Subsequently, medium containing the vector was removed followed by further culturing after adding fresh medium. 72 hours after gene introduction, culture supernatant containing the gene-recombinant lentivirus was collected. The culture supernatant was centrifuged for 5 minutes at 1700×g to remove large cell debris followed by passing the supernatant through a 0.45 μm filter (Merck-Millipore Corp., Billerica, Mass., USA) to remove fine debris. Subsequently, the supernatant was concentrated by a factor of 100 by subjecting to ultracentrifugation treatment with an ultracentrifuge (CP80β, Hitachi Koki Co., Ltd., Tokyo, Japan) for 1.5 hours under conditions of 87,000×g and 4° C. to obtain a concentrated virus used to infect human iPS cells.

(ii) Lentivirus Infection Procedure

Infection with lentivirus was carried out using a procedure obtained by modifying the method of Nakagawa, et al. (Nakagawa, M., et al., A novel efficient feeder-free culture system for the derivation of human induced pluripotent stem cells, Sci. Rep., 2014; 4: 3594). The procedures thereof are described below.

Human iPS cells were cultured to confluence in one well of a 6-well culture dish (Becton Dickinson and Company) followed by detaching the cells with CTK solution. Small cell aggregates were re-suspended in 1 mL of medium (primate ES/iPS cell medium) followed by transferring to a 15 mL centrifuge tube (Becton Dickinson and Company) and allowing to stand undisturbed at room temperature for 5 minutes. After removing 500 μL of supernatant, 400 μL of fresh medium containing 8 μg of Polybrene (Sigma-Aldrich Corp.) were added. 100 μL of concentrate virus supernatant were added followed by mixing with the cells and incubating for 6 hours at 37° C. The cells and virus suspension were occasionally agitated during the 6 hours of incubation. Cells infected with lentivirus were seeded onto SL10 neomycin-resistant feeder cells (Reprocell Inc.) seeded in two wells of the 6-well culture dish followed by culturing at 37° C. After culturing overnight, 1 mL of medium was added to the cells and the medium was replaced 36 hours after infection followed by washing away the virus particles. The cells were treated with G418 sulfate (400 μg/mL) (Invitrogen Corp.) for 36 hours 4 days after infection. Subsequently, the cells were rinsed twice with phosphate-buffered saline (PBS) to wash off the G418 sulfate followed by additionally culturing for several days. The cells were retreated with G418 sulfate as necessary.

(Induction of Myocardial Differentiation and Preparation of Cardiomyocyte Sheet Using a Bioreactor)

Induction of myocardial differentiation in the iPS cells was carried out using a bioreactor system (Able Corp., Japan) in accordance with the method of Matsuura et al., (Matsuura, K., et al., Creation of human cardiac cell sheets using pluripotent stem cells, Biochem. Biophys. Res. Commun., 2012 Aug. 24; 425(2): 321-7), see Patent Document 1). Prior to seeding the cells, the surface of a temperature-responsive culture dish (Upcell®, CellSeed Inc., Tokyo, Japan) or cell culture dish (Corning, Inc., Corning, N.Y., USA) was coated with fetal bovine serum (FBS) for 2 hours. After the iPS cells were induced to differentiate into cardiomyocytes, the cells were detached using 0.05% trypsin/EDTA and the cell aggregates were broken up into single cells using a strainer (BD Biosciences, Inc., San Jose, Calif., USA), followed by seeding in a culture dish at $2.1 \times 10^5$ cells/cm$^2$ using DMEM medium (Sigma-Aldrich Corp., St. Louis, Mo., USA) containing 10% FBS and culturing in a humidified atmosphere at 37° C. and 5% $CO_2$. In several of the experiments, the cells were treated with puromycin (Sigma-Aldrich Corp., 1.5 μg/mL) for 1 day to purify the iPS cell-derived cardiomyocytes (strain 201B7, αMHC-puro/Rex1-neo).

iPS cell-derived fibroblasts were obtained by a technique consisting of seeding the cells in a culture dish in advance (pre-plating method). Namely, after inducing the iPS cells to differentiate into cardiac muscle, the cells were seeded in an uncoated culture dish and cultured using DMEM containing 10% FBS. Subsequently, cells not adhered to the culture dish were discarded and the adhered cells were carefully washed three times with PBS(−) followed by culturing using DMEM containing 10% FBS. More than 99% of the cells were SM22-positive, and the proportion of cTnT-positive cells was less than 1%. The iPS cell-derived fibroblasts were used in the experiments after subculturing two to three times.

(Two-Dimensional Co-Culturing Test)

Cells following induction of differentiation from human iPS cells to cardiac muscle were seeded in a 24-well culture dish (Corning, Inc.) at $2.1 \times 10^5$ cells/cm$^2$ followed by culturing for 2 days in a humidified atmosphere at 37° C. and 5% $CO_2$ using DMEM containing 10% FBS. One day prior to a co-culturing experiment, iPS cells cultured on iMatrix 511 were detached with TrypLE Select followed by culturing a single cell suspension for 1 day on EZ Spheres (Asahi Glass Co., Ltd., Tokyo, Japan) using AK03 medium containing Y27632 (generic compound name, 10 μM, Wako Pure Chemical Industries, Ltd., Japan) in order to form cell aggregates. On the following day, 50 cell aggregates of iPS cells and iPS-cell derived cardiomyocytes were co-cultured for 1 day on a 24-well plate using AK03 medium. Continuing, co-culturing was carried out for 2 days each under conditions of 37° C. (AK03 medium), 42° C. (AK03 medium), 37° C. (10% PBS-containing DMEM) or 42° C. (10% FBS-containing DMEM).

(Co-Culturing Test Using Bioreactor)

iPS cells cultured on MEF were detached as single cells using Accumax (Innovative Cell Technologies Inc., San Diego, Calif., USA). $2 \times 10^7$ iPS cells (containing MEF) and cardiomyocytes on day 12 following induction of differentiation to cardiac muscle were co-cultured using a 100 mL bioreactor and mTeSR1 medium (STEMCELL Technologies Corp., Canada) containing Y27632 (10 μM) (Day 0). On the following day, the medium was replaced with mTeSR1 medium not containing Y27632. Two days after the start of co-culturing (Day 2), the cells were cultured for 48 hours at 37° C. or cultured for 42 hours at 37° C. after culturing for 6 hours at 42° C. (total of 48 hours) in mTeSR1 medium. Four days after the start of culturing (Day 4), cells cultured under the respective conditions were detached with Accumax and re-seeded at $2.1 \times 10^1$ cells/cm$^2$ in 24-well culture dishes pre-coated with FBS followed by culturing at 37° C. using DMEM containing 10% FBS and fixing with 4% paraformaldehyde for FACS analysis. The cells in the culture dishes were again cultured for 2 days at 42° C. (from Day 5 to Day 7) followed by culturing for 1 day at 37° C. (from Day 7 to Day 8).

(Immunocytochemistry)

The cells were fixed with 4% paraformaldehyde and immunostained according to the method of Matsuura et al. (Matsuura, K., et al., Creation of human cardiac cell sheets using pluripotent stem cells, Biochem. Biophys. Res. Commun., 2012 Aug. 24; 425(2): 321-7). Staining was carried out in accordance with the manual using the Click-IT TUNEL Alexa Fluor 488 imaging kit (Life Technologies Corp., California, USA) in order to carry out TUNEL analysis. The cell nuclei were stained with Hoechst 33258 (Sigma-Aldrich Corp.). Stained samples were photographed using ImageExpress (Molecular Devices, LLC, Sunnyvale, Calif., USA) and MetaXpress and AcuityXpres software (Molecular Devices, LLC).

(RNA Extraction and Quantitative RT-PCR)

Total RNA extraction and RT-PCR were carried out in accordance with the method of Matsuura, K. and Kodama, F., et al. (Matsuura, K., Kodama, F., et al., Elimination of remaining undifferentiated iPS cells in the process of human cardiac cell sheet fabrication using a methionine-free culture condition, Tissue Eng. Part C: Methods, 2014 Sep. 23). The primer pairs and Taqman probes used were the same as those used in the aforementioned method of Matsuura, K. and Kodama, F. et al. Detailed primer data is shown in Table 1 and all of the primers used were purchased from Life Technologies Corp. Quantitative PCR was carried out using the 7300 Real-Time PCR System (Applied Biosystems, Inc.). Relative mRNA expression levels were calculated using a standard curve of the mRNA expression level of GAPDH or β-actin.

TABLE 1

Primer Data

| Gene Name | ABI No. |
| --- | --- |
| POUF51 (OCT3/4) | Hs00999632_g1 |
| Lin28 | Hs00702808_s1 |
| Myosin, light chain 2, regulatory, cardiac, slow (MYL2) | Hs00166405_m1 |
| Myosin, light chain 7, regulatory (MYL7) | Hs01085598_g1 |
| Troponin T type 2 (cardiac) (TNNT2) | Hs00165960_m1 |
| Collagen type I alpha 1 (COL1A1) | Hs00164004_m1 |
| Collagen type III alpha 1 (COL3A1) | Hs00943809_m1 |
| Natriuretic peptide A (NPPA) | Hs00383230_g1 |
| Natriuretic peptide B (NPPB) | Hs01057466_g1 |
| TRPV-1 | Hs00218912_m1 |
| GAPDH | Hs00266705_g1 |
| Actin, beta | Hs99999903_m1 |

(Flow Cytometry Analysis)

Cell aggregates under each of the conditions were detached for 10 minutes at 37° C. using Accumax followed by staining Tra-1 60 or cardiac muscle troponin T (cTnT) according to the method of Matsuura, et al. (Matsuura, K., et al., Creation of human cardiac cell sheets using pluripotent stem cells, Biochem. Biophys. Res. Commun., 2012 Aug. 24; 425(2): 321-7). The proportions of the cells were analyzed using Gallios (Beckman Coulter Inc., Brea, Calif., USA) and Cell Quest Pro Version 5.2 software.

(TRPV-1 Knockdown)

iPS cells cultured on iMatrix 511 were transfected with TRPV-1 siRNA (Life Technologies Corp., catalog no.: 4392240) and a negative control (Life Technologies Corp., Silencer® Select Negative Control No. 1 siRNA, product no: 4390843) using Lipofectamine® RNAi Max Transfection Reagent (Life Technologies Corp.) in accordance with the manual.

(TRPV-1 Agonists)

The following reagents were used as TRPV-1 agonists.
Capsaicin (Sigma-Aldrich Corp.)
Arvanil (Wako Pure Chemical Industries, Ltd.)
OLDA (Tocris Bioscience)
Vehicle: Ethanol (Wako Pure Chemical Industries, Ltd.)

(Statistical Analysis)

Data was expressed as the mean±standard deviation. Statistical analysis when comparing two groups was carried out using the Student's t-test. Statistical analysis when comparing multiple groups was carried out using the one-way analysis of variance, and comparisons were tested with Dunnett's test. A p-value of less than 0.05 was considered to be statistically significant.

Example 1

Figure 2:
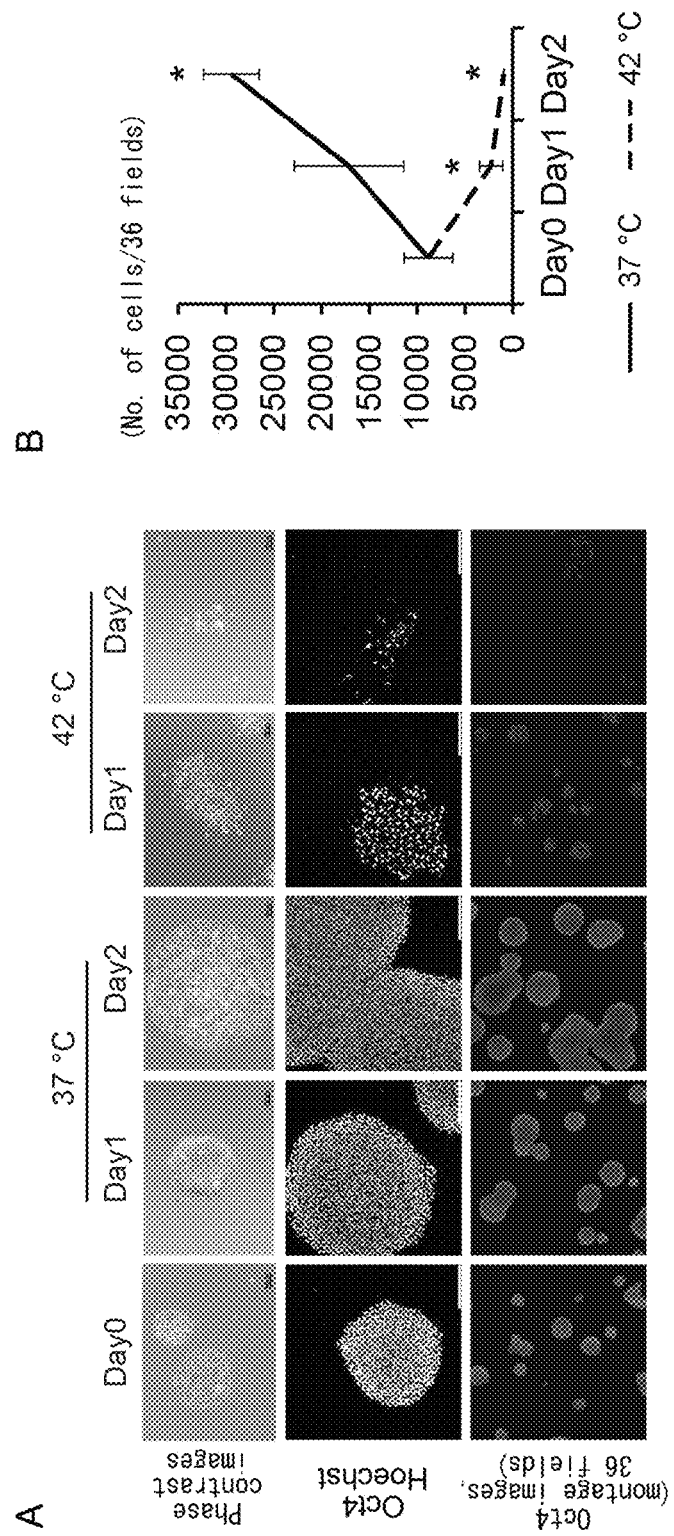
FIG. 2 indicates the numbers of feeder-less iPS cells cultured at 42° C.

In order to confirm whether or not a high culture temperature causes damage to iPS cells, iPS cells cultured on laminin E8 fragments were cultured for 1 or 2 days under conditions of 37° C., 40° C., 41° C. or 42° C. (FIGS. 1A and 1B). The numbers of iPS cells cultured at 37° C. and 40° C. increased significantly dependent on the duration of culturing (37° C.: Day 0: 10311±1395, Day 1: 23748±1611, Day 2: 41563±760; 40° C.: Day 1: 21758±3219, Day 2:

40706±591). It is interesting to note that growth of iPS cells cultured at 41° C. was interrupted on Day 1 (13228±2037) and the number of cells decreased on Day 2 (4278±848). However, the number of iPS cells cultured at 42° C. decreased significantly dependent on the duration of culturing (Day 1: 2459±934, Day 2: 1216±229). Accompanying these changes, the number of iPS cells expressing Oct4 increased considerably at 37° C. (Day 0: 8834±2545, Day 1: 17134±5731, Day 2: 31100±2894), while the number of iPS cells expressing Oct4 cultured at 42° C. decreased significantly (Day 1: 2271±1208, Day 2: 961±26 (FIG. 2). Accompanying this decrease in the number of cells at 42° C., the number of TUNEL-positive cells increased significantly dependent on the duration of culturing (Day 0: 3.4±0.2, Day 1: 9.4±4.1, Day 2: 33.0±5.6) (FIGS. 1C and 1D). On the basis of these results, a temperature of 42° C. was suggested to be an important temperature for causing apoptosis in human iPS cells. These cytotoxic effects at 42° C. were similarly observed in a different iPS cell line (line 1231A3) cultured in the absence of feeder cells.

Figure 3:
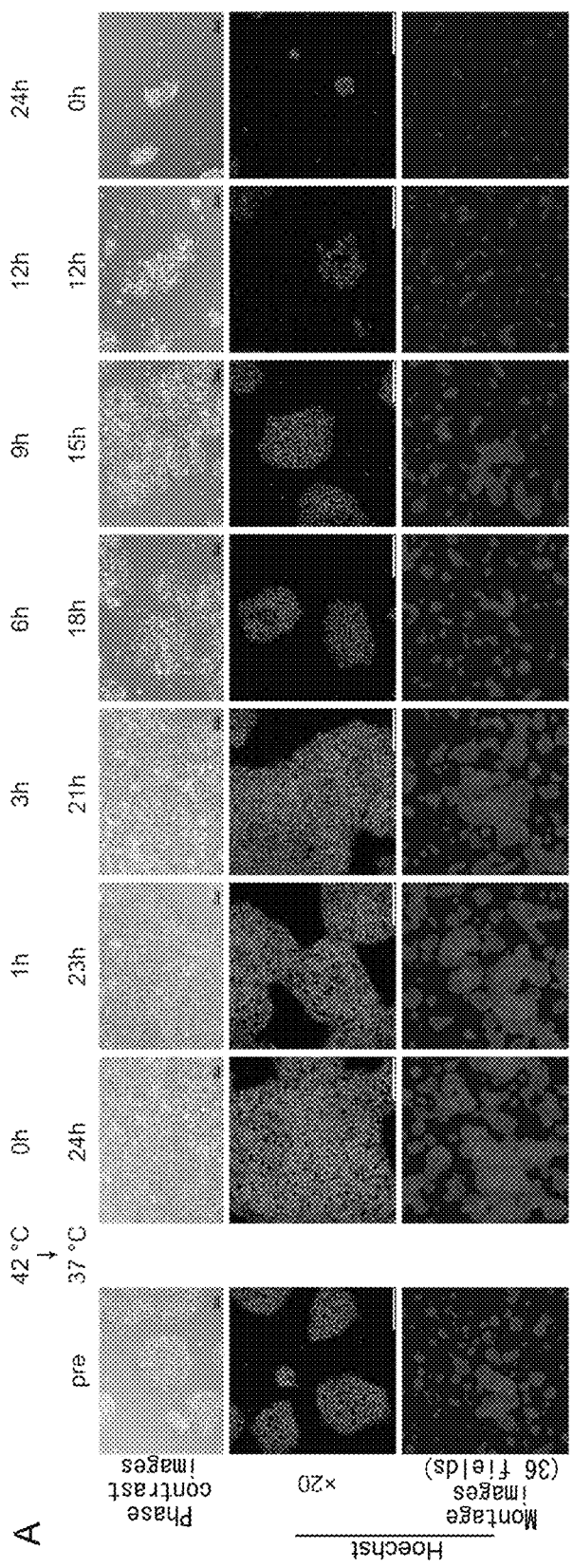
FIG. 3 illustrates the effects of culture temperature on human iPS cells cultured under feeder-less conditions. iPS cells cultured on laminin E8 fragments were cultured at 42° C. for 1 hour, 3 hours, 6 hours, 9 hours or 12 hours followed by culturing at 37° C. until 24 hours after the start of culturing.
Figure 3:
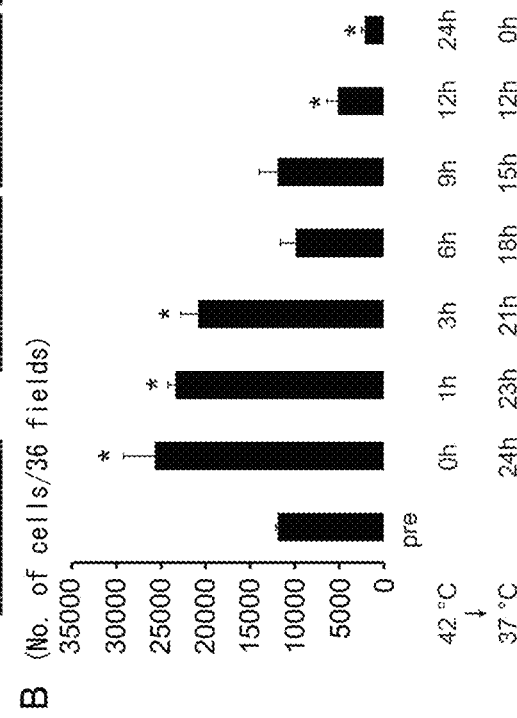

Next, the minimum culturing time at 42° C. at which iPS cells die was confirmed. iPS cells were cultured for 1 hour or 3 hours at 42° C. followed by culturing at 37° C. up to 24 hours after the respective start of culturing. The numbers of cells increased significantly in comparison with the numbers of cells on Day 0 for both culturing times in the same manner as when culturing for 24 hours at 37° C. (prior to start of culturing: 11897±207; 37° C., 24 hours: 25721±3477; 42° C., 1 hour+37° C., 23 hours: 23391±842; 42° C., 3 hours+37° C., 21 hours: 20834±1942) (FIGS. 3A and 3B). There were hardly any changes in the numbers of cells in the case of having cultured for 6 hours and 9 hours at 42° C. (42° C., 6 hours+37° C., 18 hours: 9909±1714; 42° C., 9 hours+37° C., 15 hours: 11934±2032). However, the numbers of cells deceased significantly in comparison with Day 0 in the case of having cultured for 12 hours or more at 42° C. (42° C., 12 hours+37° C., 12 hours: 5172±1168; 42° C., 24 hours: 2160±332). On the basis of these results, culturing at 42° C. for 12 hours or more was suggested to have the potential for being important for reducing iPS cells (FIGS. 3A and 3B).

Figure 4:
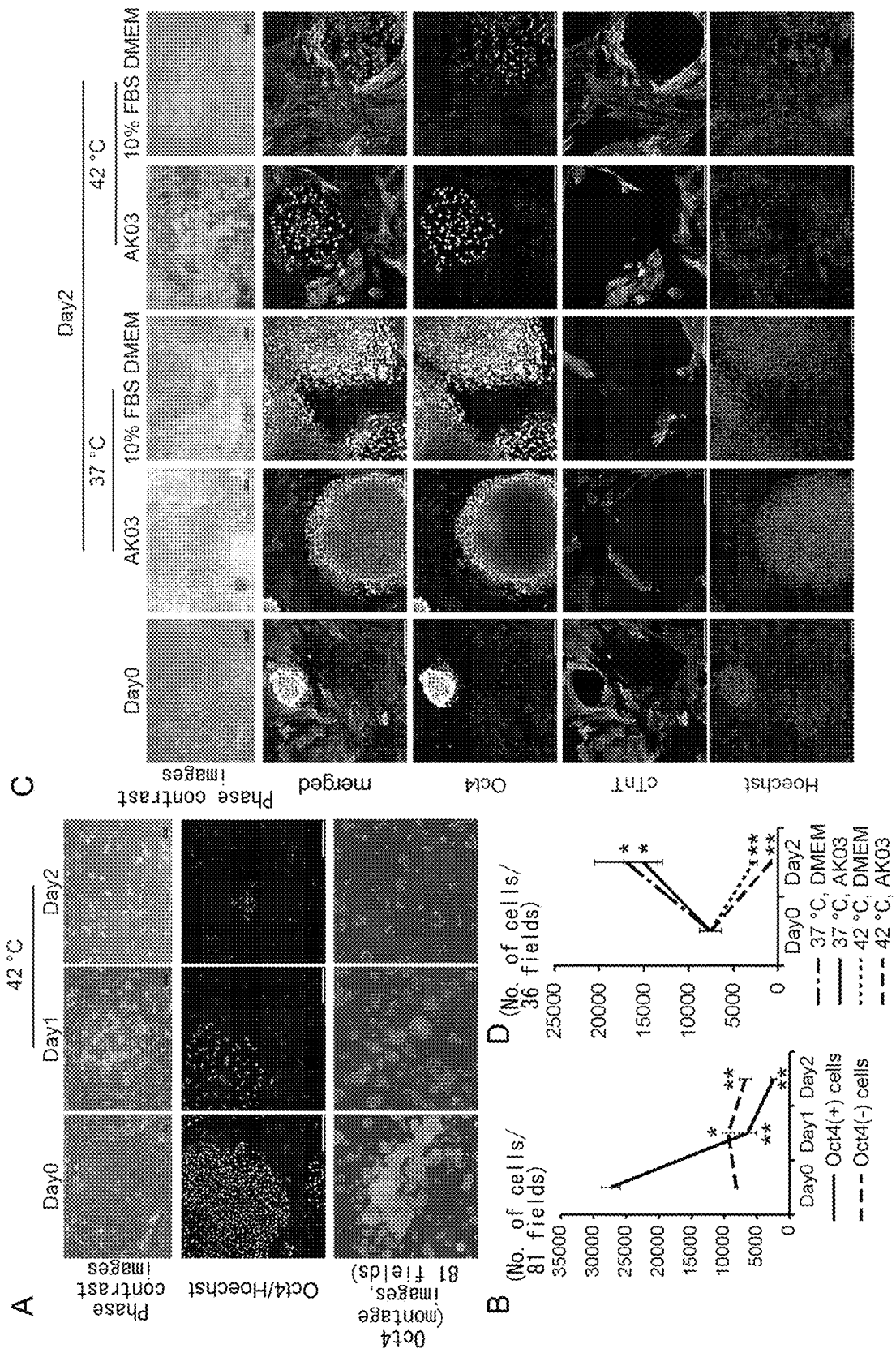
FIG. 4 illustrates the effects of culturing at 42° C. during co-culturing of iPS cells with other cells.

Since feeder cells also have the potential for allowing cell survival through interaction with iPS cells, whether or not a culture temperature of 42° C. is effective against iPS cells cultured on MEF was determined in order to confirm the effects of feeder cells. When iPS cells cultured on MEF were cultured at 42° C., although many of the cells that formed colonies died out by Day 2, cells surrounding the colonies remained (FIG. 4A). According to the results of confocal high-content image analysis, although the number of Oct4-positive cells decreased significantly dependent on the duration of culturing (Day 0: 9931±250, Day 1: 5250±1866, Day 2: 767±215), the number of Oct4-negative cells clearly underwent hardly any change through Day 2 (Day 0: 11323±1835, Day 1: 11843±925, Day 2: 12967±1440) (FIGS. 4A and 4B). These findings suggest that, although a temperature of 42° C. imparts cytotoxicity to iPS cells, it has no effect on differentiated cells in the manner of feeder cells. Since it is possible that there are differences in the interaction between cells of different types, it is important to determine whether or not residual iPS cells are eliminated at 42° C. in bioengineered tissues used in regenerative medicine. When aggregates of iPS cells were co-cultured for 1 day with iPS cell-derived cardiomyocytes, the iPS cells took to the cardiomyocytes (Day 0: 7531±1229) (FIGS. 4C and 4D). When these co-cultured cells were further cultured for 2 days at 37° C. in iPS cell medium (AK3) or cardiomyocyte medium (DMEM containing 10% FBS), the cells proliferated considerably, colony size increased, and cardiomyocytes were arranged around the colonies (Day 2 (AK03): 15065±2166, Day 2 (DMEM): 16984±3520) (FIGS. 4C and 4D). On the other hand, when the aforementioned co-cultured cells were cultured for 2 days at 42° C., the number of Oct4-positive cells decreased and iPS cells were only sparsely present in the colonies (Day 2 (AK03): 790±66, Day 2 (DMEM): 2730±421) (FIGS. 4C and 4D). According to these results, iPS cells were suggested to be able to be eliminated by culturing at 42° C. even under conditions of co-culturing with cells of various cell types.

Example 2

It is necessary to confirm the manner in which culturing under conditions of 42° C. affects differentiated cells used in bioengineered tissue in order to apply the method for reducing iPS cells of the present invention in regenerative medicine applications. Since cardiomyocyte sheets derived from human iPS cells are mainly composed of cardiomyocytes, fibroblasts and the like, the manner in which culturing under conditions of 42° C. affects iPS cell-derived cardiomyocytes and fibroblasts was confirmed.

Figure 5:
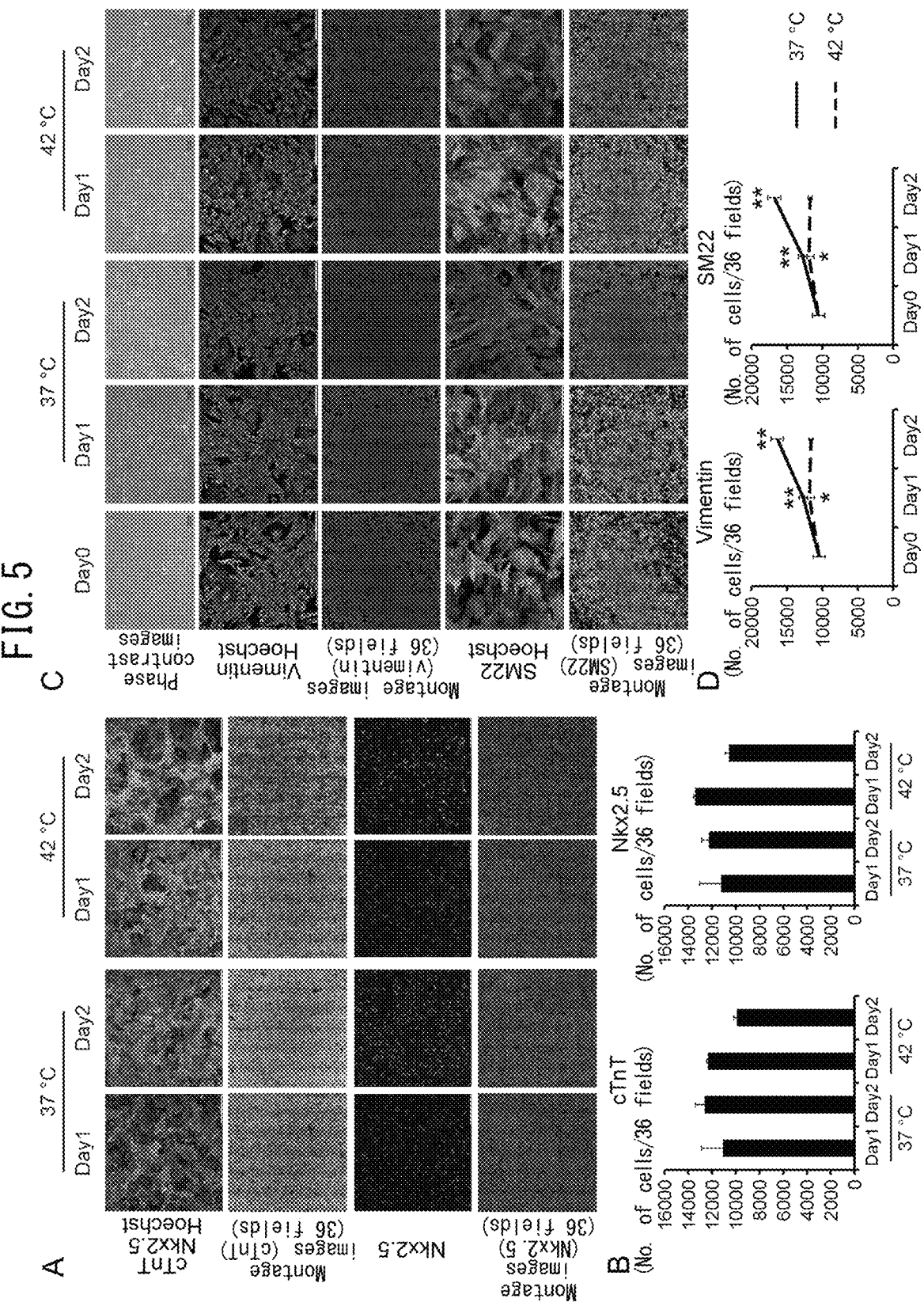
FIG. 5 illustrates confirmation of the effects of temperature on iPS cell-derived cardiomyocytes and fibroblasts.

When iPS cell-derived cardiomyocytes were cultured under conditions of 37° C. or 42° C., the cardiomyocytes demonstrated independent pulsation, and many of the cells survived even under conditions of culturing for 2 days at 37° C. and 42° C. In the case of having cultured at 37° C. and 42° C. for one day (Day 1) or two days (Day 2), there were hardly any changes in the numbers of cTnT-positive and Nkx2.5-positive cardiomyocytes (cTnT-positive cells: 37° C. (Day 1): 11084±1810, 37° C. (Day 2): 12625±768, 42° C. (Day 1): 12343±105, 42° C. (Day 2): 9917±252; Nkx2.5-positive cells: 37° C. (Day 1): 11249±1783, 37° C. (Day 2): 12272±607, 42° C. (Day 1): 13432±105, 42° C. (Day 2): 10586±309) (FIGS. 5A and 5B). These results suggest that cardiomyocytes are also resistant to culturing under conditions of 42° C.

Next, the effects of culturing under conditions of 42° C. on fibroblasts derived from iPS cells were investigated. When iPS cell-derived fibroblasts were cultured at 37° C., the number of fibroblasts derived from vimentin-positive or SM22-positive iPS cells increased significantly in comparison with Day 0 (vimentin-positive: Day 0: 10451±835, Day 1: 12686±593, Day 2: 16353±868; SM22-positive: Day 0: 10553±876, Day 1: 12777±615, Day 2: 16752±940) (FIGS. 5C and 5D). On the other hand, although the number of iPS cell-derived fibroblasts increased significantly on Day 1 when cultured at 42° C. (vimentin-positive: 11818±689; SM22-positive: 11895±693) (FIGS. 5C and 5D), there were no significant differences on Day 2 (vimentin-positive: 11592±293; SM22-positive: 11738±278) (FIGS. 5C and 5D). These findings suggested the possibility that iPS cell-derived fibroblasts are also resistant to culturing at 42° C.

Figure 6:
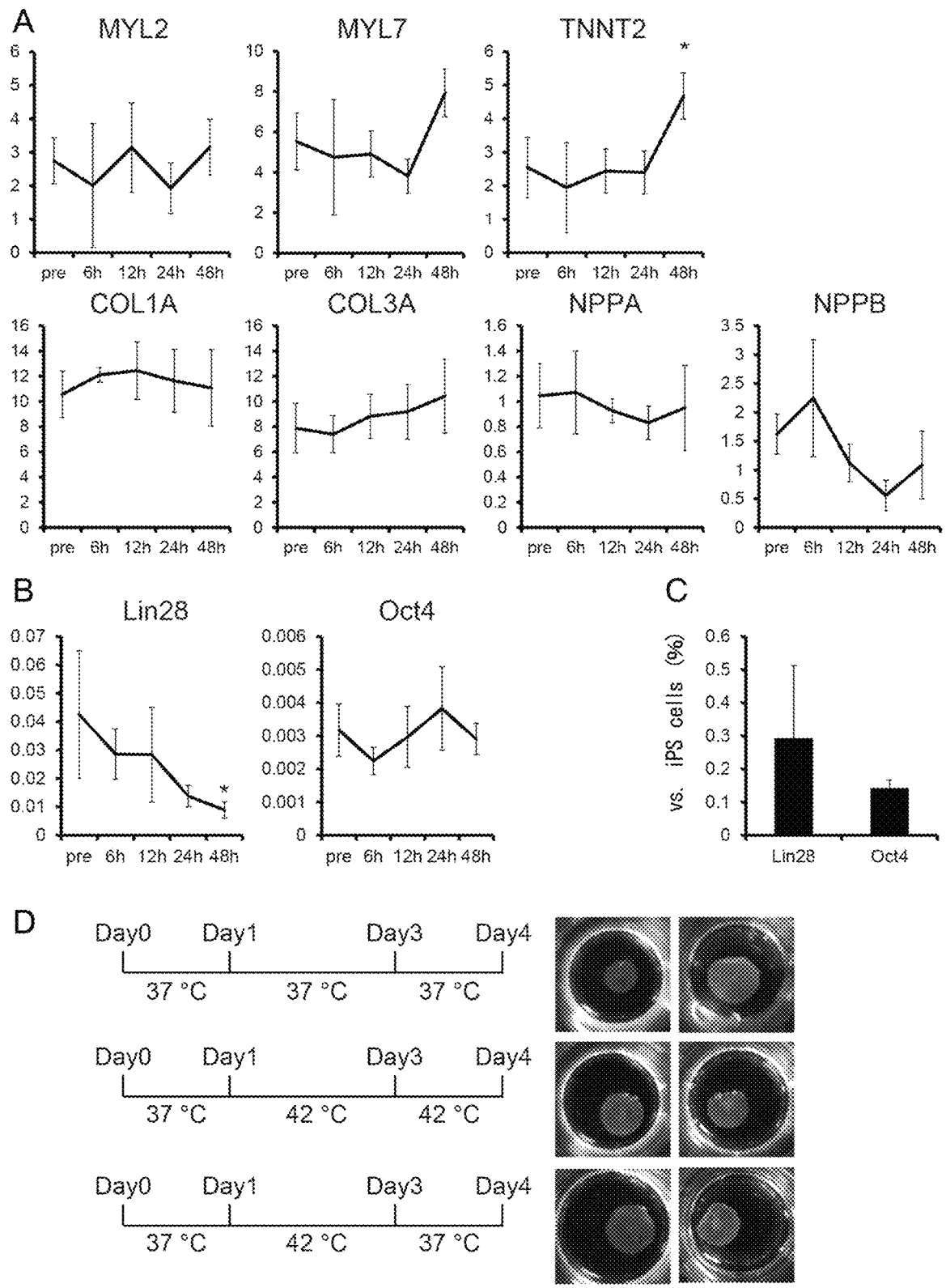
FIG. 6 depicts the effect of eliminating iPS cells in the fabrication of cardiomyocyte sheets.

Expression of mRNA of heart muscle and extracellular matrix genes was analyzed to investigate the types of effects of a temperature of 42° C. on gene expression of iPS cell-derived cardiomyocytes and fibroblasts. In the case of having cultured iPS cells containing cardiomyocytes and fibroblasts at 42° C., although expression of mRNA of MYL2, MYL7, Col1A, Col3A, NPPA and NPPB did not change up to 48 hours, the expression level of TNNT2 increased significantly (FIG. 6A). This suggested that transcription activity is maintained even under culturing conditions of 42° C. In contrast to these results, when cultured at 42° C., the expression level of Lin28 in iPS cell-derived cardiomyocytes decreased significantly (FIG. 6B), and the expression level of Lin28 of cells cultured for 48 hours at 42° C. was roughly 0.3% the expression level of iPS cells (FIG. 6C). On the basis thereof, culturing at 42° C. was indicated to be extremely useful for reducing residual iPS cells present in cells derived from iPS cells.

Although culturing at 42° C. has hardly any effect on iPS cell-derived cardiomyocytes, it is important to determine what types of effects culturing at 42° C. have on the construction of bioengineered tissue used in regenerative medicine. iPS cell-derived cardiomyocytes following induction of differentiation into cardiac muscle were confirmed to demonstrate independent pulsation when cultured for 4 days in a temperature-responsive culture dish, and a single-layer cell sheet was fabricated when the culture temperature was lowered (FIG. 6D). It is interesting to note that cell sheets were obtained even if the culture temperature was lowered after having cultured the iPS cell-derived cardiomyocytes at 42° C. for 2 days (from Day 1 to Day 3) or for 3 days (from Day 1 to Day 4) (FIG. 6D). This suggests that various constituents required for the construction of bioengineered tissue containing intercellular junction protein, basement membrane protein and extracellular matrix are maintained even when cultured at 42° C. However, in the case of having cultured at 42° C. for three days (from Day 1 to Day 4), myocardial pulsation occasionally became weak. On the other hand, in the case of having cultured at 42° C. for two days (from Day 1 to Day 3), there was no effect on myocardial pulsation. On the basis thereof, culturing for two days at 42° C. during the course of fabricating cell sheets was suggested to have the possibility of constituting optimal conditions for eliminating residual iPS cells without having an effect on the survival rate of cardiomyocytes.

Example 3

(TRPV-1-Mediated Elimination of Residual iPS Cells in Human Myocardial Tissue)

Figure 7:
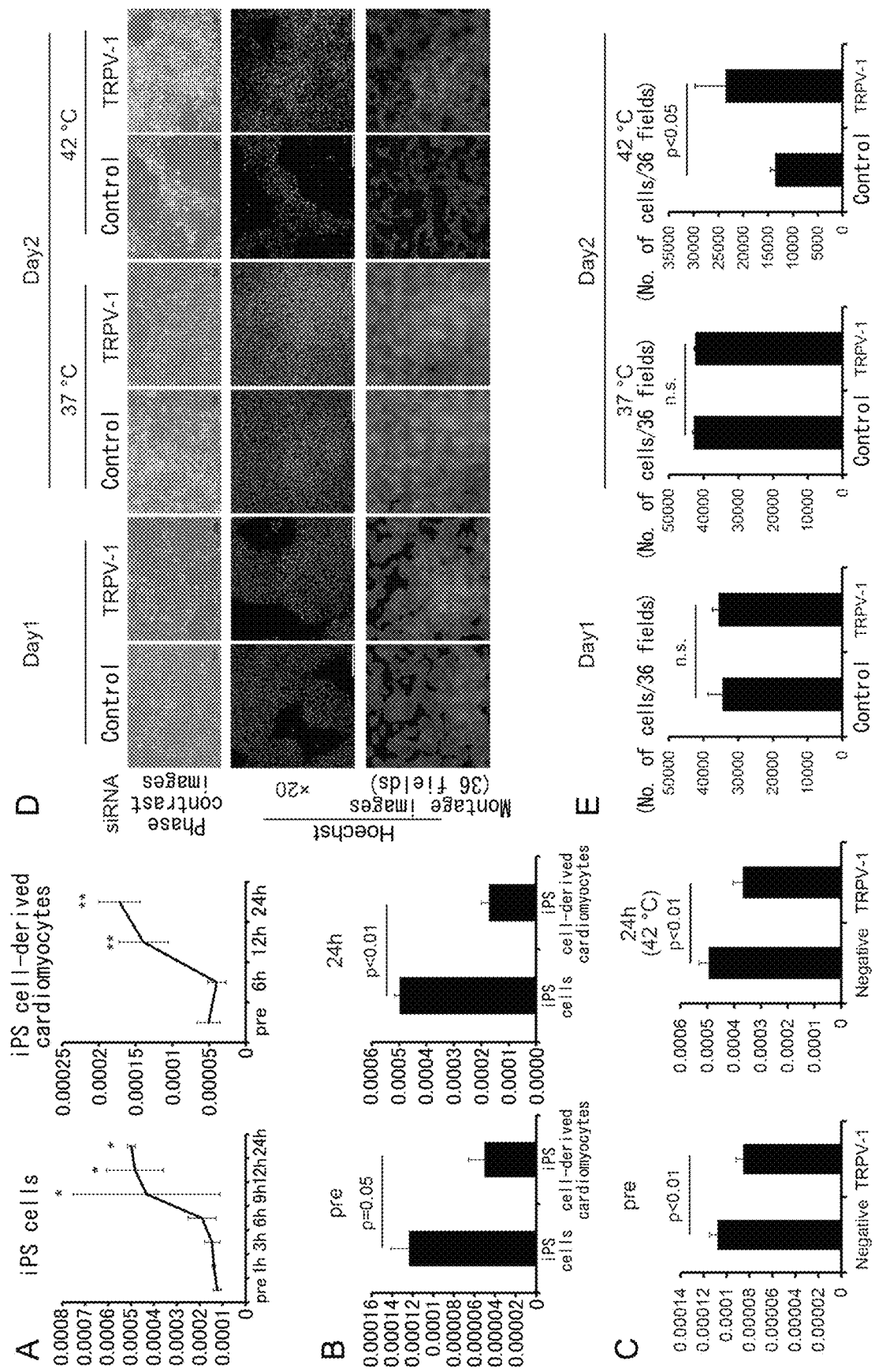
FIG. 7 illustrates the reduction of iPS cells by culturing at 42° C. mediated by TRPV-1.

High-temperature conditions are known activate the temperature-sensitive TRP channel, transient receptor potential vanilloid 1 (TRPV-1). We next determined that TRPV-1 is expressed in iPS cells and iPS-derived cardiomyocytes. The expression level of TRPV-1 mRNA of iPS cells increased significantly in the case of having cultured for 9 hours at 42° C., and the expression level of TRPV-1 mRNA of iPS-derived cardiomyocytes increased after culturing for 12 hours at 42° C. (FIG. 7A). On the other hand, the expression level of TRPV-1 was significantly higher for iPS cells than baseline (before culturing at 42° C.) iPS cell-derived cardiomyocytes and iPS cell-derived cardiomyocytes cultured at 42° C. for 24 hours (FIG. 7B). These results may explain the finding that differences in TRPV-1 activity attributable to culturing at 42° C. have different degrees of elimination efficacy on iPS cells and iPS cell-derived cardiomyocytes cultured at 42° C.

In order to confirm whether the cytotoxic effects of culturing at 42° C. on iPS cells are attributable to interaction with TRPV-1, iPS cells were transfected with siRNA against TRPV-1. The increase in the expression level of TRPV-1 occurring concomitantly to culturing at 42° C. was able to be confirmed to be inhibited by knockdown of TRPV-1 (FIG. 7C), and in accordance therewith, the reduction in the number of iPS cells following culturing at 42° C. was also inhibited by transfection of siRNA (FIGS. 7D and 7E). On the basis of these results, TRPV-1 was suggested to play an important role in the elimination of iPS cells during culturing at 42° C.

Figure 8:
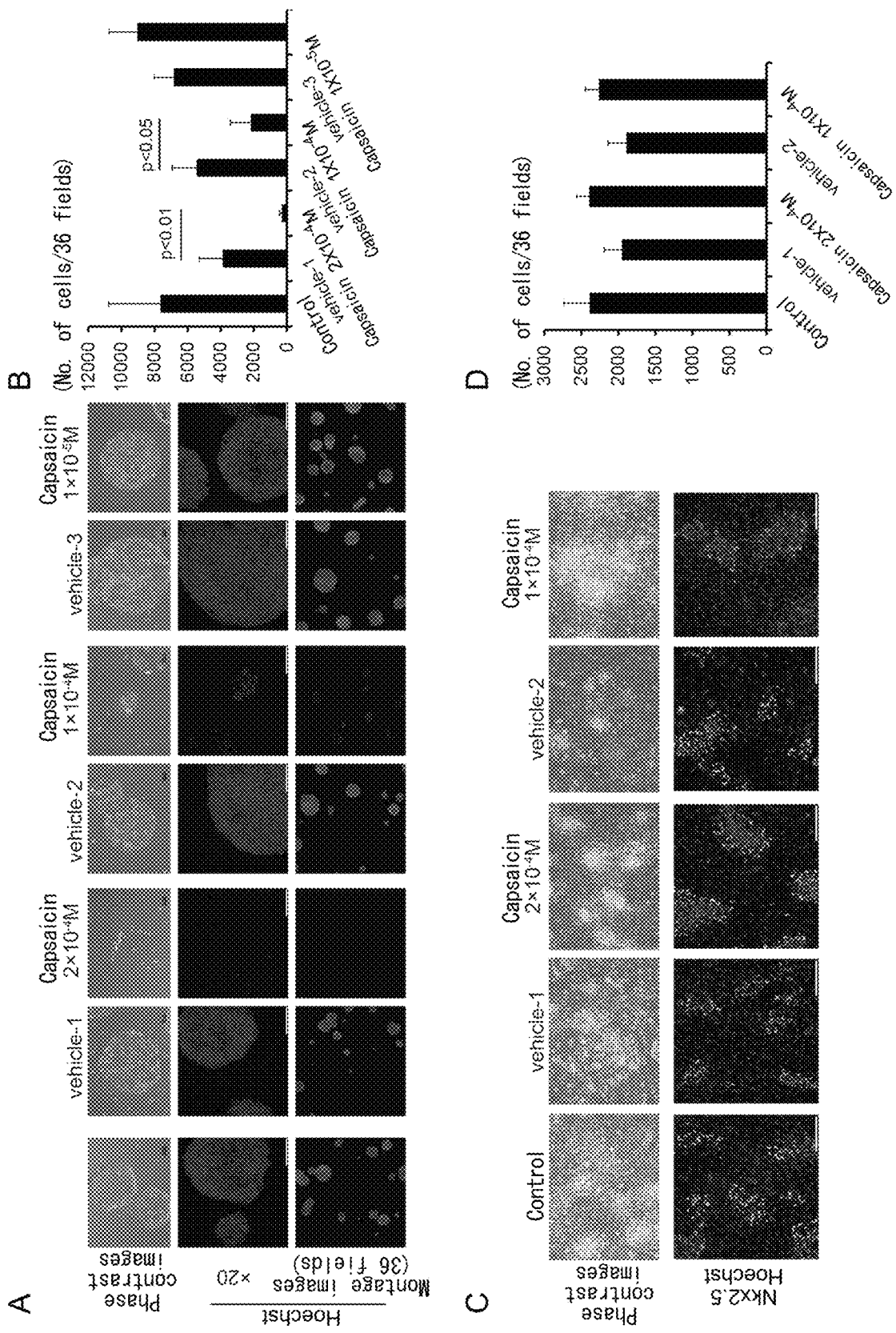
FIG. 8 illustrates the effect of eliminating iPS cells using TRPV-1 agonists.
Figure 9:
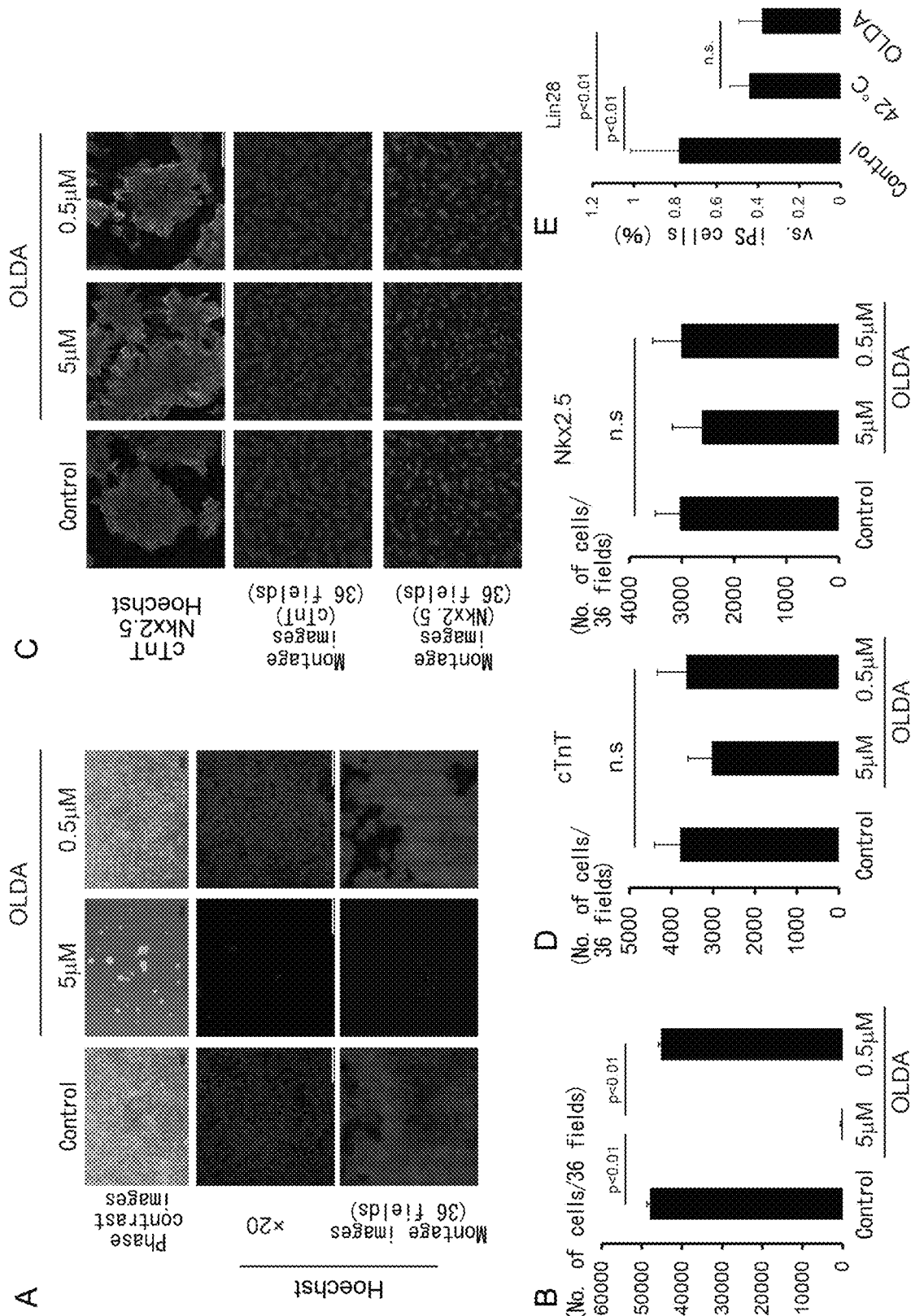
FIG. 9 illustrates the effect of eliminating iPS cells using TRPV-1 agonists.
Figure 10:
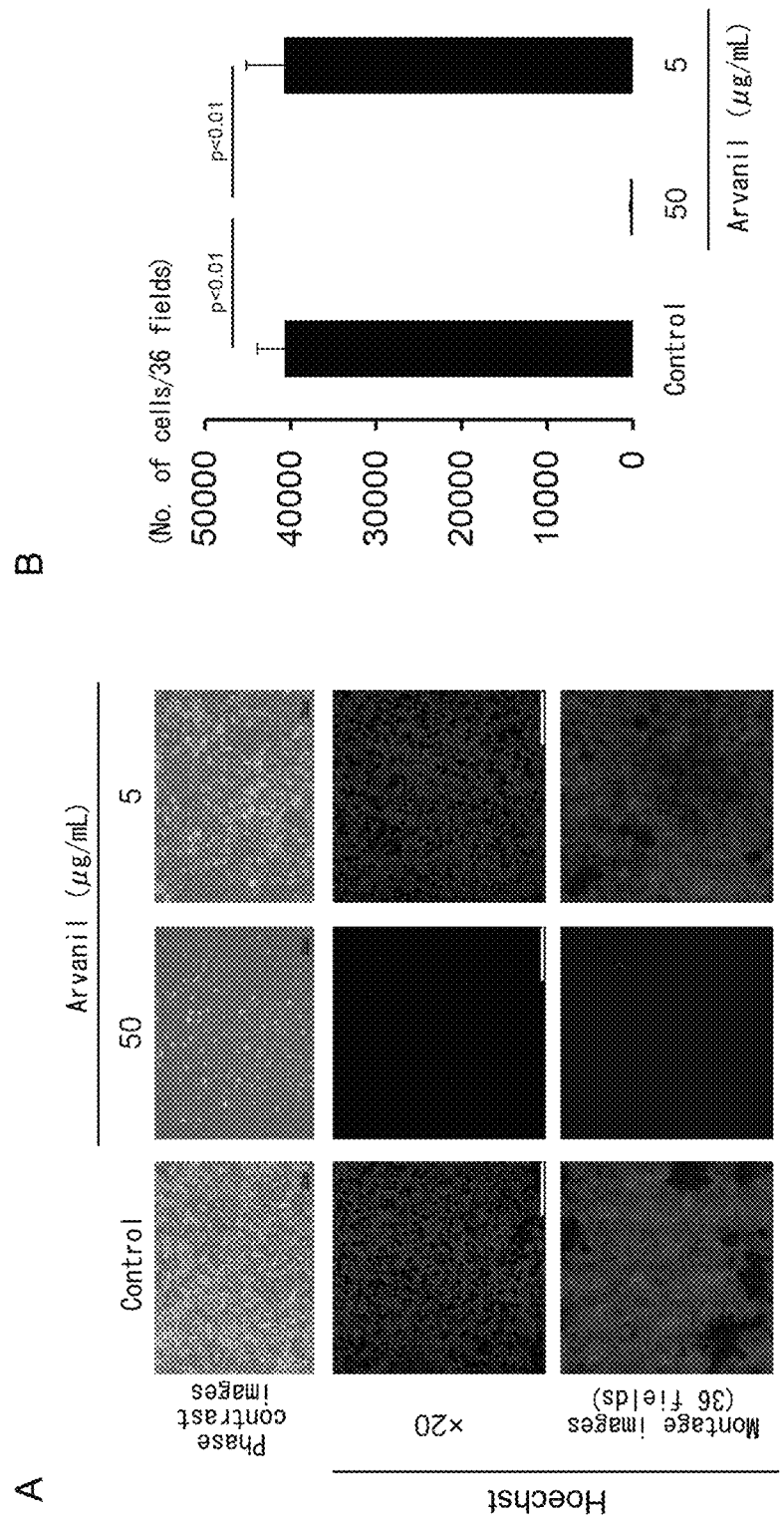
FIG. 10 illustrates the effect of eliminating iPS cells using TRPV-1 agonists.

Finally, whether or not pharmacological activity of TRPV-1 has a cytotoxic effect on iPS cells, and whether or not there is an effect on cardiomyocytes, were confirmed. When feeder-less iPS cells were cultured with TRPV-1 agonists including capsaicin (FIG. 8), OLDA (FIG. 9) and arvanil (FIG. 10), the number of cells significantly decreased concentration-dependently in the case of using capsaicin (FIGS. 8A and 8B), and treatment with the other TRPV-1 agonists also demonstrated cytotoxic activity against iPS cells (FIGS. 9 and 10). Conversely, when iPS cell-derived cardiomyocytes were cultured in medium containing capsaicin at concentrations toxic to iPS cells (200 μM and 100 μM), independent pulsation of the cardiomyocytes was maintained and there were no changes in the numbers of Nkx2.5-positive cells from that when cultured in the vehicle (FIGS. 8C and 8D). On the basis thereof, TRPV-1 agonists were suggested to be effective for reducing iPS cells without having an effect on the survival rate of cardiomyocytes.

INDUSTRIAL APPLICABILITY

According to the method indicated in the present invention, undifferentiated pluripotent stem cells can be reduced from a cell population obtained by inducing differentiation of a cell population containing pluripotent stem cells. Such a cell population has the potential for lowering the risk of tumorigenesis when used as a graft material in fields such as regenerative medicine, thereby making it industrially useful. In addition, the method of the present invention is also useful in that it enables undifferentiated pluripotent stem cells to be simply and inexpensively eliminated from differentiated cell populations derived from pluripotent stem cells used in experimental and other applications.

The invention claimed is:

1. A method for reducing pluripotent stem cells from a cell population containing pluripotent stem cells and differentiated cells derived from pluripotent stem cells, comprising:
a step for activating TRPV-1 expressed in the pluripotent stem cells contained in the cell population, wherein the step for activating TRPV-1 is:
a step for activating the TRPV-1 by culturing at a temperature of 41.5° C. or higher, for 10 hours to 72 hours, to thereby reduce the pluripotent stem cells from the cell population.

2. The method according to claim 1, wherein the temperature is 41.5° C. to 43° C.

3. The method according to claim 1, wherein the pluripotent stem cells are induced pluripotent stem cells and/or embryonic stem cells.

4. The method according to claim 1, wherein the differentiated cells are cardiomyocytes, cardiomyoblasts, fibroblasts, parietal cells and/or vascular endothelial cells.

* * * * *